United States Patent
Pecinovsky

(10) Patent No.: US 12,187,945 B1
(45) Date of Patent: Jan. 7, 2025

(54) FERROELECTRIC NEMATIC COMPOSITION AND DEVICE THEREOF

(71) Applicant: Polaris Electro-Optics, Inc., Boulder, CO (US)

(72) Inventor: Cory Pecinovsky, Lafayette, CO (US)

(73) Assignee: POLARIS ELECTRO-OPTICS, INC., Boulder, CO (US)

( * ) Notice: Subject to any disclaimer, the term of this patent is extended or adjusted under 35 U.S.C. 154(b) by 0 days.

(21) Appl. No.: 18/353,000

(22) Filed: Jul. 14, 2023

Related U.S. Application Data

(60) Provisional application No. 63/389,314, filed on Jul. 14, 2022.

(51) Int. Cl.
| | | |
|---|---|---|
| *G02F 1/135* | (2006.01) | |
| *C07C 205/57* | (2006.01) | |
| *C07C 245/08* | (2006.01) | |
| *C07C 255/57* | (2006.01) | |
| *C07D 319/06* | (2006.01) | |
| *C07D 405/08* | (2006.01) | |
| *C09K 19/02* | (2006.01) | |
| *C09K 19/20* | (2006.01) | |
| *C09K 19/24* | (2006.01) | |
| *C09K 19/34* | (2006.01) | |

(52) U.S. Cl.
CPC ........ *C09K 19/3402* (2013.01); *C07C 205/57* (2013.01); *C07C 245/08* (2013.01); *C07C 255/57* (2013.01); *C07D 319/06* (2013.01); *C07D 405/08* (2013.01); *C09K 19/0225* (2013.01); *C09K 19/2007* (2013.01); *C09K 19/24* (2013.01); *C09K 19/3477* (2013.01); *G02F 1/135* (2013.01); *C09K 2019/2035* (2013.01); *C09K 2019/2078* (2013.01); *C09K 2019/3422* (2013.01)

(58) Field of Classification Search
CPC .... G02F 1/135; G02F 1/141; G02F 1/133348; C09K 19/3402; C09K 19/0225; C09K 19/2007; C09K 19/24; C09K 19/3477; C09K 2019/2035; C09K 2019/2078; C09K 2019/3422; C07C 205/57; C07C 245/08; C07C 255/57; C07D 319/06; C07D 405/08

See application file for complete search history.

(56) References Cited

FOREIGN PATENT DOCUMENTS

WO    WO-2023034628 A2 *  3/2023    ......... C09K 19/0225

\* cited by examiner

*Primary Examiner* — Thoi V Duong
(74) *Attorney, Agent, or Firm* — Thorpe North & Western, LLP; David W. Osborne

(57) ABSTRACT

Provided herein are ferroelectric nematic ($N_F$) compositions comprising a ferroelectric nematic host and one or more nonlinear optical compounds (chromophores).

20 Claims, 2 Drawing Sheets

FERROELECTRIC NEMATIC COMPOSITION AND DEVICE THEREOF

CROSS-REFERENCE TO RELATED APPLICATIONS

This application claims the benefit of U.S. Provisional Application No. 63/389,314, filed Jul. 14, 2022, which is incorporated herein by reference in its entirety.

BACKGROUND

Materials that have a ferroelectric nematic ($N_F$) phase were discovered and found to have unique electro-optics properties, e.g., having a permanent electric polarization density in the absence of applied field. See, e.g., Chen et al., *Proc. Natl. Acad. Sci. U.S.A.* 117 (25): 14021-14031 (2020). The polarization of such ferroelectric nematic host material is comparable to that of solid-state ferroelectrics, and the coupling of the electric field to the large macroscopic polarization can result in orders of magnitude faster molecular reorientation when comparing to conventional nematics. The combination of spontaneous non-centrosymmetric ordering, large molecular dipoles and polarizability along the dipole axis, and easy alignment of $N_F$ materials over large areas confers large second order nonlinear optical susceptibilities ($\chi^{(2)}$) to these fluids, and opens a realm of electro-optic applications previously unaccessible to liquid crystals.

Applications of materials with large $\chi^{(2)}$ include second harmonic generation and the linear electro-optic effect (Pockels effect), which have been historically reserved for inorganic ferroelectric crystals (e.g., $LiNbO_3$, $KH_2PO_4$). Organic ferroelectrics offer the possibility of engineering materials with ultra-large $\chi^{(2)}$ and $N_F$ fluids may allow alignment of the polar axis over very large volumes.

SUMMARY OF THE DISCLOSURE

A facile approach to increasing $\chi^{(2)}$ of $N_F$ materials can be achieved by using the $N_F$ phase to template the polar alignment of nonlinear optical (NLO) chromophores (e.g., as a dopant). NLO chromophores also have large molecular dipoles and can be designed to be highly compatible with $N_F$ materials, resulting in high loadings with preservation of the $N_F$ ordering and large macroscopic polarizations.

In one aspect, provided herein are ferroelectric nematic ($N_F$) compositions comprising a ferroelectric nematic host and a nonlinear optical compound having a formula of: D-B-A, wherein D is a donor moiety, B is a π-conjugated bridging moiety, and A is an acceptor moiety; wherein the second order nonlinear optical (NLO) coefficient of the nonlinear optical compound is higher than the NLO coefficient of the $N_F$ host.

In some embodiments, the spontaneous polarization (Ps) of the ferroelectric nematic composition is greater than about 1 μC/cm^2.

In some embodiments, the spontaneous polarization (Ps) of the ferroelectric nematic composition is greater than about 1, or 10 μC/cm^2.

In some embodiments, the spontaneous polarization (Ps) of the ferroelectric nematic composition is greater than about 1, 10, or 100 μC/cm^2.

In certain embodiments, the spontaneous polarization (Ps) of the ferroelectric nematic composition is greater than about 1, 2, 3, 4, 5, 6, 7, 8, 9, 10, 20, 30, 40, 50, 60, 70, 80, 90 or 100 μC/cm^2.

In certain embodiments, the NLO coefficient of the NF host is greater than 0.1, 0.2, 0.3, 0.4, 0.5, 0.6, 0.7, 0.8, 0.9, or 1 pm/V.

In certain embodiments, the NLO coefficient of the NF host is greater than 1 pm/V.

In certain embodiments, the dipole moments (μ) of the NF host is greater than about 5 D, 6 D, 7 D, 8 D, 9 D, or 10 D.

In certain embodiments, the dipole moments (μ) of the NF host is greater than about 11 D, 12 D, 13 D, 14 D, 15 D, 16 D, 17 D, 18 D, 19 D, 20 D, 25 D, 30 D, 35 D, 40 D, or 45 D.

In certain embodiments, the NF host is not a polymer.

In certain embodiments, the NF host comprises a compound of Formula (I):

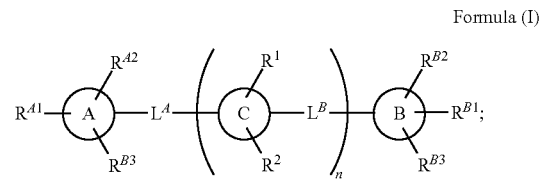

Formula (I)

wherein ring A, ring B, and each ring C are independently an aryl;

$L^A$ and each $L^B$ are each independently a bond, —N=N—, or

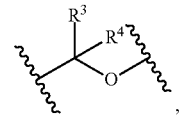

wherein $R^3$ and $R^4$ are each fluoro or $R^3$ and $R^4$ form an oxo;

$R^1$ and $R^2$ are each independently hydrogen, fluoro, or $C_{1-6}$ alkoxy;

$R^{A1}$ is hydrogen, $C_{1-6}$ alkyl, $C_{1-6}$ alkoxy, $C_{1-6}$ heteroalkyl, or

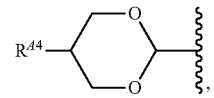

wherein $R^{A4}$ is $C_{1-6}$ alkyl;

$R^{A2}$ and $R^{A3}$ are each independently hydrogen, fluoro, or —OR, wherein R is $C_{1-6}$ alkyl optionally substituted with a $C_{1-6}$ alkoxy;

$R^{B1}$ is fluoro, —$NO_2$, or —CN;

$R^{B2}$ and $R^{B3}$ are each independently hydrogen, fluoro, or methoxy; and n is an integer of 1 to 8;

provided at least one of $L^A$ and $L^B$ is not a bond.

In certain embodiments, the compound of Formula (I) has a structure of Formula (Ia):

Formula (Ia)

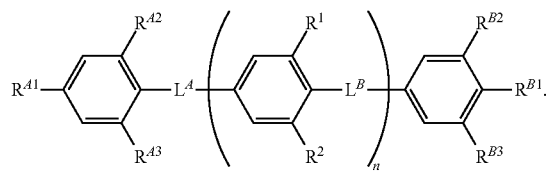

In certain embodiments, the compound of Formula (I) has a structure of Formula (Ib):

Formula (Ib)

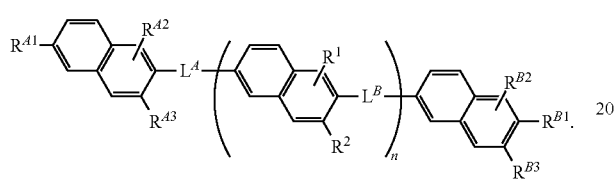

In certain embodiments, the compound of Formula (I) has a structure of Formula (Ib'):

Formula (Ib')

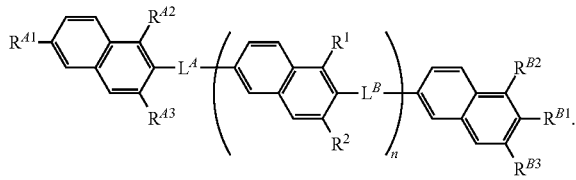

In certain embodiments, $L^A$ and each $L^B$ are

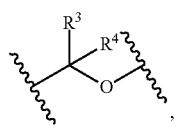

wherein $R^3$ and $R^4$ are each fluoro or $R^3$ and $R^4$ form an oxo.

In certain embodiments, $L^A$ and each $L^B$ are

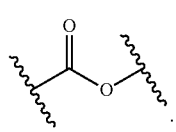 [SMILES: *OC(*)=O]

In certain embodiments, $L^A$ is a bond and each $L^B$ is

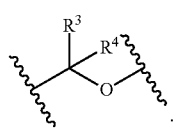

In certain embodiments, $L^A$ is a bond and each $L^B$ is —$CF_2O$—.

In certain embodiments, $L^A$ is

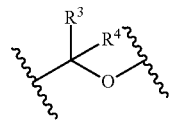

and each $L^B$ is a bond.

In certain embodiments, $L^A$ is

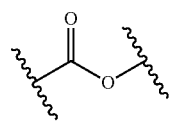 [SMILES: *OC(*)=O]

and each $L^B$ is a bond.

In certain embodiments, $L^A$ is

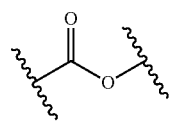 [SMILES: *OC(*)=O]

and each $L^B$ is —N=N—.

In certain embodiments, $R^1$ and $R^2$ are each hydrogen.
In certain embodiments, $R^1$ and $R^2$ are each fluoro.
In certain embodiments, $R^1$ is hydrogen and $R^2$ is $C_{1-6}$ alkoxy.
In certain embodiments, $R^1$ is hydrogen and $R^2$ is n-propoxy.

In certain embodiments,

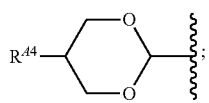

$R^{A1}$ is $C_{1-6}$ alkyl or

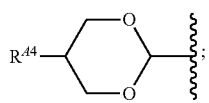

wherein $R^X$ is $C_{1-6}$ alkyl and $R^Y$ is $C_{1-6}$ alkyl optionally substituted with methoxy. In certain embodiments,

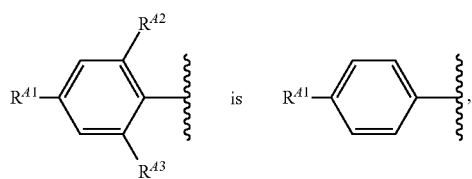 is 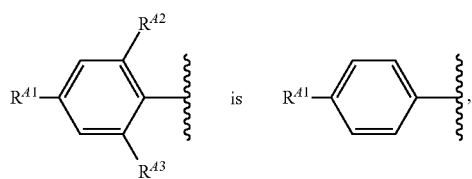, wherein $R^{A1}$ is methoxy. In certain embodiments,

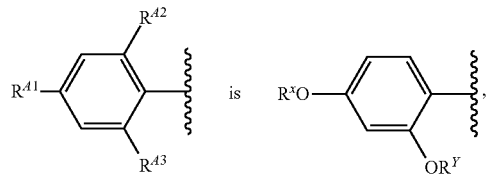 is 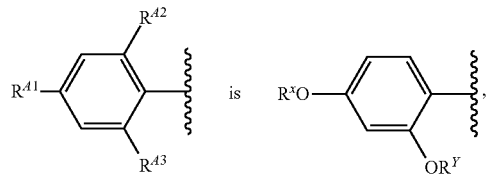, and $R^X$ is methyl or ethyl, and $R^Y$ is methyl, ethyl, n-propyl, or methoxyethyl. In certain embodiments,

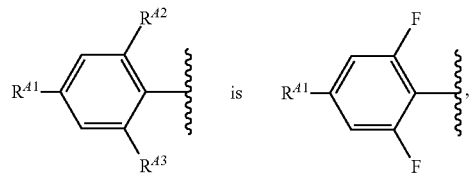 is 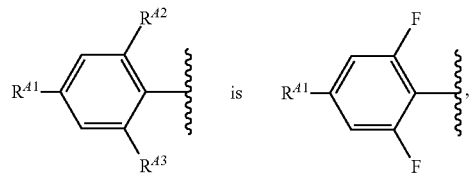, $R^{A1}$ is $C_{1-6}$ alkyl,

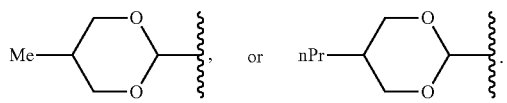

In certain embodiments,

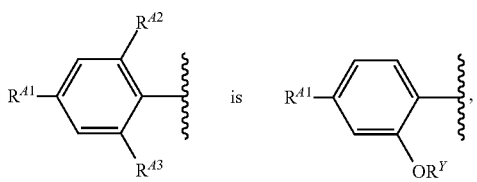 is 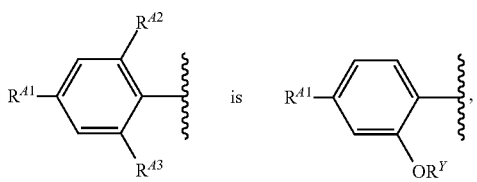, $R^{A1}$ is hydrogen, $C_{1-6}$ alkyl, $C_{1-6}$ alkoxy, $C_{1-6}$ heteroalkyl, or

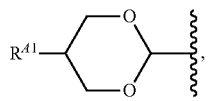, and $R^{A4}$ is $C_{1-6}$ alkyl, $R^Y$ is $C_{1-6}$ alkyl optionally substituted with a $C_{1-6}$ alkoxy.

In some embodiments,

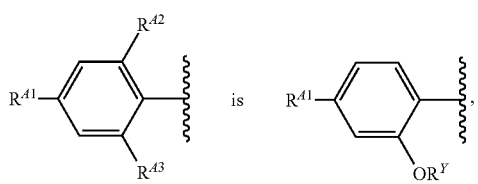 is 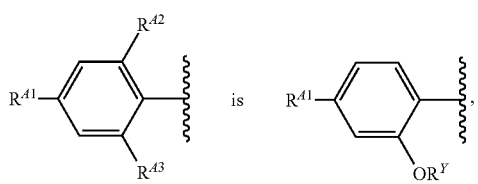, and $R^{A1}$ is $C_{1-6}$ alkyl, $C_{1-6}$ alkoxy, or $C_{1-6}$ heteroalkyl. In some embodiments, $R^{A1}$ is $C_{1-6}$ alkyl, —O—($C_{1-6}$ alkyl), or —N($C_{1-6}$ alkyl)($C_{1-6}$ alkyl). In some embodiments, $R^{A1}$ is —N($C_{1-6}$ alkyl)($C_{1-6}$ alkyl). In some embodiments, $R^{A1}$ is —N(Me)$_2$. In some embodiments, $R^{A1}$ is —N(Et)$_2$.

In certain embodiments,

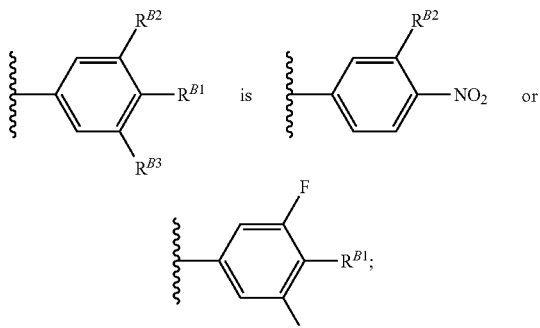

wherein $R^{B2}$ is hydrogen or fluoro, and $R^{B1}$ is —CN or F. In certain embodiments,

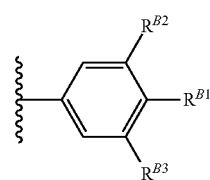

is

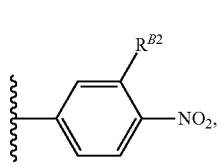, wherein $R^{B2}$ is hydrogen or fluoro. In certain embodiments,

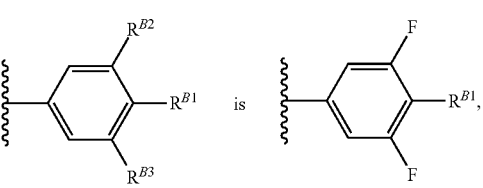

wherein $R^{B1}$ is —CN or F.

In certain embodiments, the $N_F$ host is a polymer.

In certain embodiments, the $N_F$ host is a polymer having a recurring unit of Formula (II):

Formula (II)

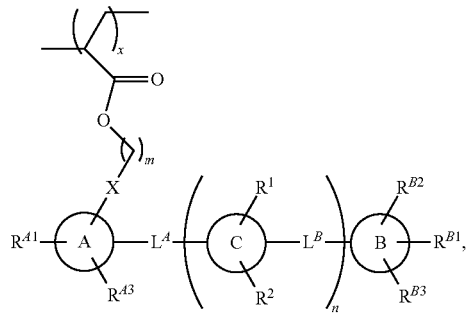

wherein ring A, ring B, and each ring C are independently an aryl;

$L^A$ and each $L^B$ are independently a bond, —N=N—, or

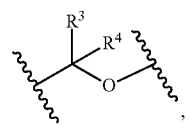

wherein $R^3$ and $R^4$ are each fluoro or $R^3$ and $R^4$ form an oxo;

$R^1$ and $R^2$ are each independently hydrogen, fluoro, or $C_{1-6}$ alkoxy;

$R^{A1}$ is hydrogen, $C_{1-6}$ alkyl, $C_{1-6}$ alkoxy, or

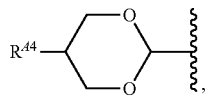

wherein $R^{A4}$ is $C_{1-6}$ alkyl;

$R^{A2}$ and $R^{A3}$ are each independently hydrogen, fluoro, or —OR, wherein R is $C_{1-6}$ alkyl optionally substituted with a $C_{1-6}$ alkoxy;

$R^{B1}$ is fluoro, —NO$_2$, or —CN;

$R^{B2}$ and $R^{B3}$ are each independently hydrogen, fluoro, or methoxy;

n is an integer of 1 to 8;

x is an integer of 1 to 100;

at least one of $L^A$ and $L^B$ is not a bond; and

X is O or $NR^N$, wherein $R^N$ is hydrogen, —OH, benzyl, or $C_{1-6}$ alkyl; and m is an integer of 1 to 30.

In certain embodiments, the compound of Formula (II) is a compound having a Formula (IIa):

Formula (IIa)

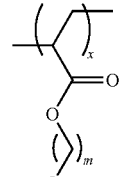
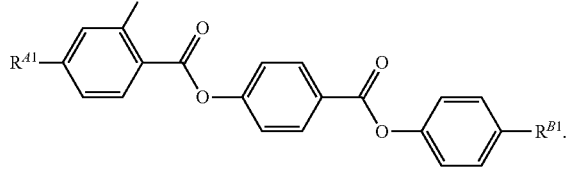

In certain embodiments, the compound of Formula (II) is:

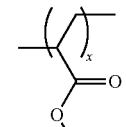
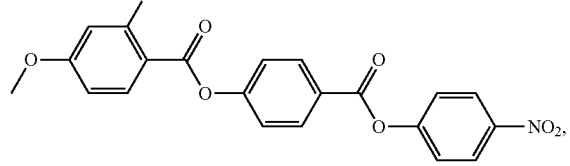

wherein m is 6.

In certain embodiments, the nonlinear optical compound has a neutral ground state.

In certain embodiments, in the nonlinear optical compound of Formula D-B-A, D is

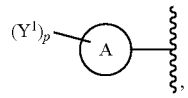

wherein Ring A is an aryl or heteroaryl ring, each $Y^1$ is independently -OH, fluoro, $NR^5R^6$ or $C_{1-6}$ alkoxy, wherein $R^5$ and $R^6$ are each independently hydrogen or $C_{1-6}$ alkyl;

p is an integer of 0 to 5.

In certain embodiments, D is selected from:

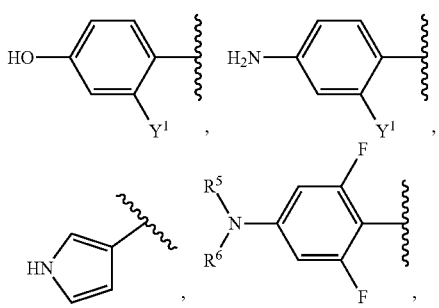

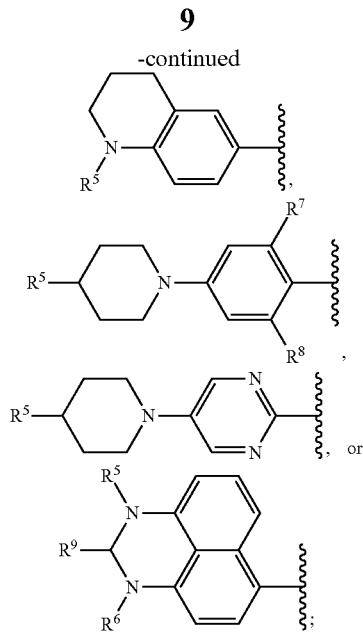

wherein $R^5$, $R^6$ and $R^9$ are each independently hydrogen or $C_{1-6}$ alkyl, and $R^7$ and $R^8$ are each independently hydrogen or $C_{1-6}$ alkoxy.

In some embodiments, in the nonlinear optical compound of Formula D-B-A, D is:

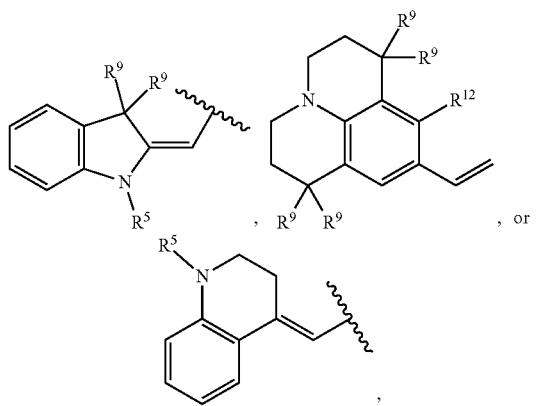

wherein $R^5$, $R^6$ and $R^9$ are each independently hydrogen or $C_{1-6}$ alkyl, and $R^{12}$ is hydrogen, $C_{1-10}$ alkyl, $C_{1-10}$ heteroalkyl, —O—$C_{1-10}$ alkyl, —O—$C_{1-10}$ heteroalkyl, —O—$C_{0-9}$ alkylene-$C_{6-10}$ aryl, —O—$C_{0-9}$ alkylene-$C_{1-10}$ heteroaryl, or —NR$^5$R$^6$.

In some embodiments, in the nonlinear optical compound of Formula D-B-A, D is:

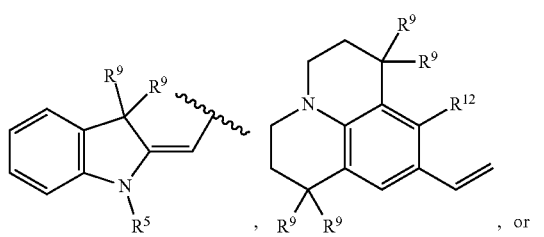

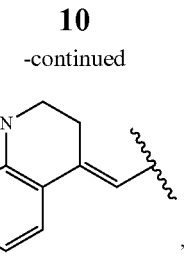

wherein $R^5$, $R^6$ and $R^9$ are each independently hydrogen, methyl, or ethyl, and $R^{12}$ is hydrogen, $C_{1-6}$ alkyl, $C_{1-6}$ heteroalkyl, —O—$C_{1-6}$ alkyl, —O—$C_{1-6}$ heteroalkyl, —O—$C_{0-6}$ alkylene-$C_{6-10}$ aryl, or —O—$C_{0-6}$ alkylene-$C_{1-10}$ heteroaryl.

In some embodiments, in the nonlinear optical compound of Formula D-B-A, D is:

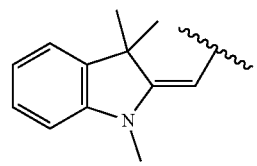

In certain embodiments, in the nonlinear optical compound of Formula D-B-A, B is selected from:

a bond

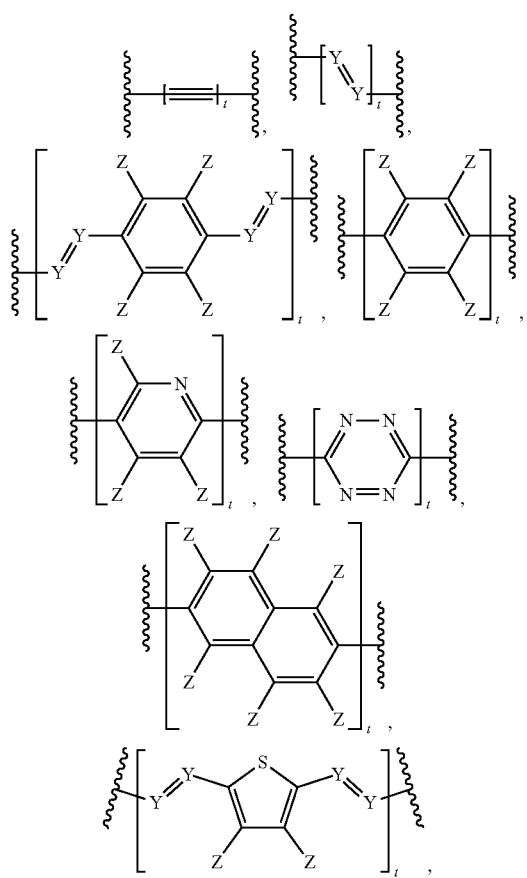

-continued

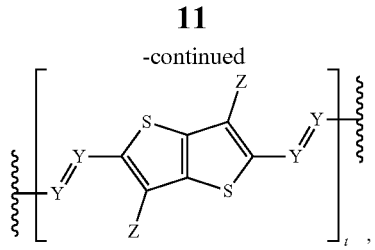

and a combination thereof; wherein each Y is independently —N= or —CH=, each Z is independently hydrogen, fluoro, chloro, or $C_{1-6}$ alkoxy, and t is an integer of 1 to 4.

In some embodiments, in the nonlinear optical compound of Formula D-B-A, B is:

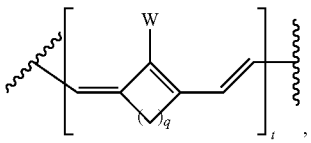

wherein W is hydrogen, fluoro, chloro, $C_{1-8}$ alkyl, $C_{1-8}$ alkoxy, $C_{1-8}$ heteroalkyl, or $C_{1-8}$ haloalkyl, q is an integer of 0 to 5, and t is an integer of 1 to 4.

In some embodiments, q is 1, 2, 3, or 4. In some embodiments, q is 1. In some embodiments, q is 2. In some embodiments, q is 3. In some embodiments, q is 4.

In some embodiments, in the nonlinear optical compound of Formula D-B-A, B is:

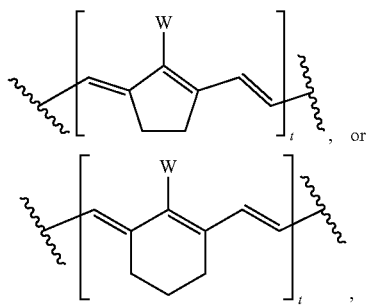

and t is an integer of 1 to 4.

In some embodiments, W is $C_{1-8}$ alkyl, $C_{1-8}$ heteroalkyl, or $C_{1-8}$ haloalkyl. In some embodiments, W is $C_{1-8}$ alkyl. In some embodiments, W is $C_{1-8}$ heteroalkyl. In some embodiments, W is $C_{1-8}$ haloalkyl. In some embodiments, W is —S—($C_{1-8}$ alkyl), —O—($C_{1-8}$ alkyl), or —N($C_{1-8}$ alkyl)($C_{1-8}$ alkyl). In some embodiments, W is —S-(butyl), —S-(pentyl), -or S-(hexyl).

In certain embodiments, B is selected from:

a bond,

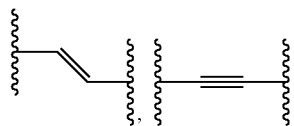

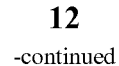

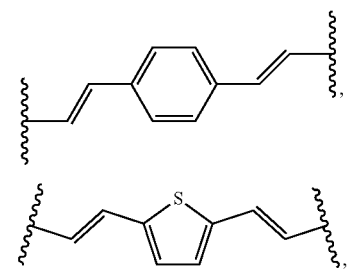

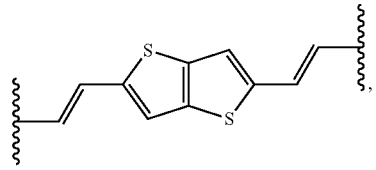

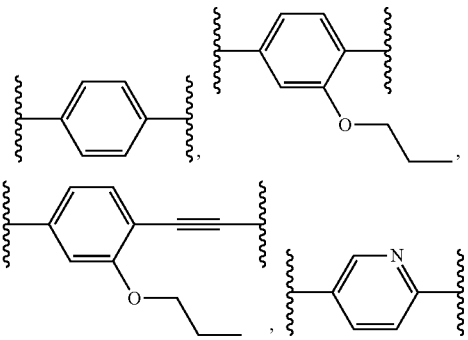

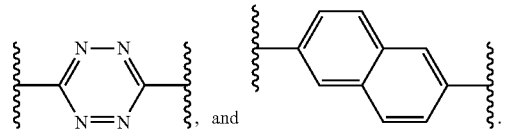, and

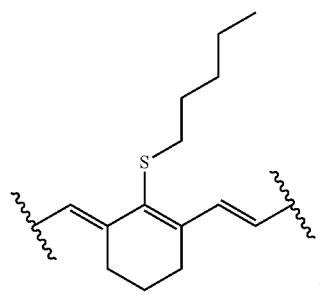

In certain embodiments, B is

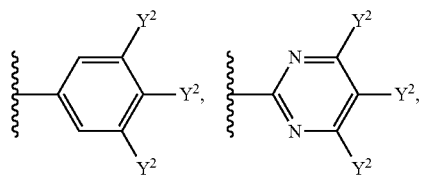

In certain embodiments, in the nonlinear optical compound of Formula D-B-A, A is selected from:

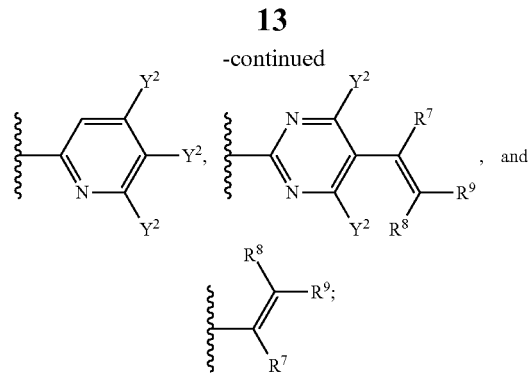

wherein each $Y^2$ is hydrogen, fluoro, chloro, —$NO_2$, —CN, —NCS, $SO_2CH_3$, or $SO_2CF_3$; $R^7$, $R^8$, and $R^9$ are each independently hydrogen or —CN, and at least one of $R^7$, $R^8$, and $R^9$ is —CN.

In certain embodiments, in the nonlinear optical compound of Formula D-B-A, A is:

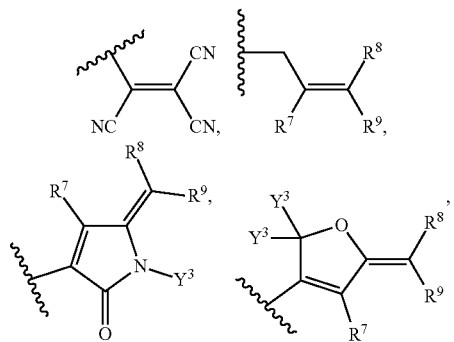

wherein each $Y^3$ is hydrogen, fluoro, chloro, $C_{1-8}$ alkyl, $C_{1-8}$ alkoxy, $C_{1-8}$ heteroalkyl, or $C_{1-8}$ haloalkyl; and $R^7$, $R^8$, and $R^9$ are each independently hydrogen or —CN, and at least one of $R^7$, $R^8$, and $R^9$ is —CN.

In some embodiments, each $Y^3$ is each independently hydrogen, fluoro, chloro, $C_{1-8}$ alkyl, or $C_{1-8}$ haloalkyl; and $R^7$, $R^8$, and $R^9$ are each independently -CN. In some embodiments, each $Y^3$ is independently $C_{1-8}$ alkoxy, $C_{1-8}$ heteroalkyl, or $C_{1-8}$ haloalkyl. In some embodiments, each $Y^3$ is each independently perfluorinated $C_{1-8}$ heteroalkyl. In some embodiments, each $Y^3$ is each independently —$CF_3$, —$CF_2CF_3$, or —$CF_2CF_2CF_3$. In some embodiments, each $Y^3$ is each independently-$CF_3$.

In certain embodiments, A is selected from:

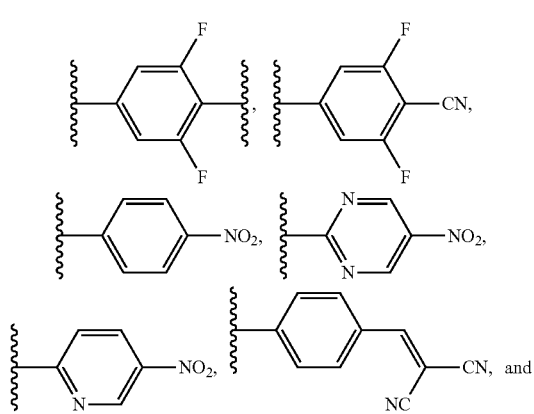

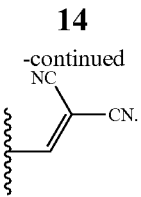

In certain embodiments, A is

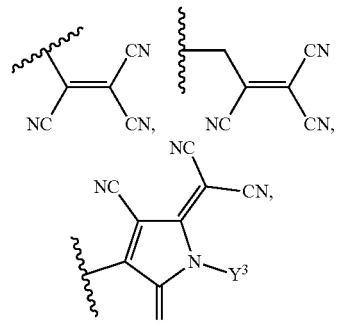

or

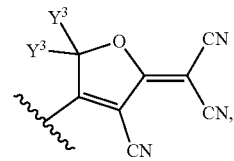

wherein each $Y^3$ is independently hydrogen, fluoro, chloro, $C_{1-8}$ alkyl, $C_{1-8}$ alkoxy, $C_{1-8}$ heteroalkyl, or $C_{1-8}$ haloalkyl.

In some embodiments, A is:

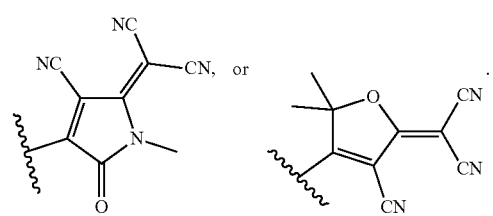 [SMILES: *C1=C(C#N)C(=C(C#N)C#N)N(C)C1=O ; *C1=C(C#N)C(=C(C#N)C#N)OC1(C)C]

In certain embodiments, the nonlinear optical compound has a zwitterionic ground state.

In certain embodiments, in the nonlinear optical compound of Formula D-B-A, D is

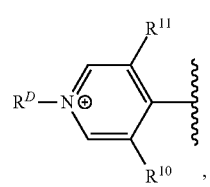

and wherein $R^{10}$ and $R^{11}$ are each independently hydrogen, fluoro, chloro, or $C_{1-6}$ alkyl; $R^D$ is $C_{1-6}$ alkyl.

In certain embodiments, in D is

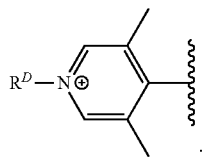

In certain embodiments, in the nonlinear optical compound of Formula D-B-A, B is selected from:

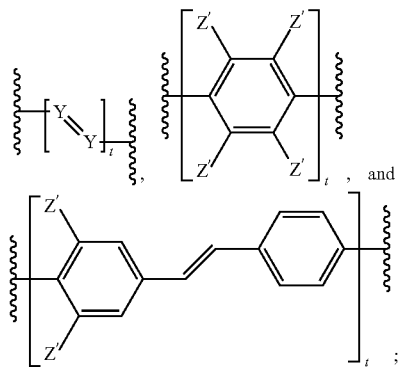

wherein each Y is independently —N= or —CH=, each Z' is independently hydrogen, fluoro, chloro, or methyl, and t is an integer of 1 to 4.

In certain embodiments, B is selected from.

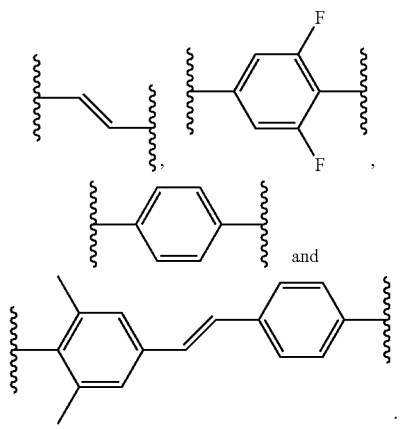

In certain embodiments, in the nonlinear optical compound of Formula D-B-A, A is

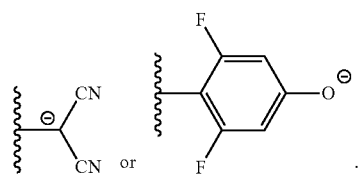

In certain embodiments, the NLO coefficient of the nonlinear optical compound is greater than 1, 2, 3, 4, 5, 10, 20, 30, 40, 50, 100, or 200 pm/V.

In certain embodiments, the NLO coefficient of the nonlinear optical compound is greater than 100 pm/V.

In certain embodiments, the NLO coefficient of the nonlinear optical compound is greater than 200 pm/V.

In certain embodiments, the ferroelectric nematic (NF) composition comprises between about 1% to about 30% w/w nonlinear optical compound(s).

In another aspect, provided herein are devices comprising the ferroelectric nematic composition described herein.

In certain embodiments, the device comprises two or more electrode.

In certain embodiments, an electric field is applied between the electrodes and across the ferroelectric nematic composition within the device.

In certain embodiments, the ferroelectric nematic (NF) compositions spontaneously form a ferroelectric polarization density and the polar axis of the ferroelectric polarization density is perpendicular to the direction of the electric field between the electrodes.

INCORPORATION BY REFERENCE

All publications, patents, and patent applications mentioned in this specification are herein incorporated by reference for the specific purposes identified herein.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings.

DETAILED DESCRIPTION

Ferroelectric Nematic ($N_F$) Compositions

Figure 1:
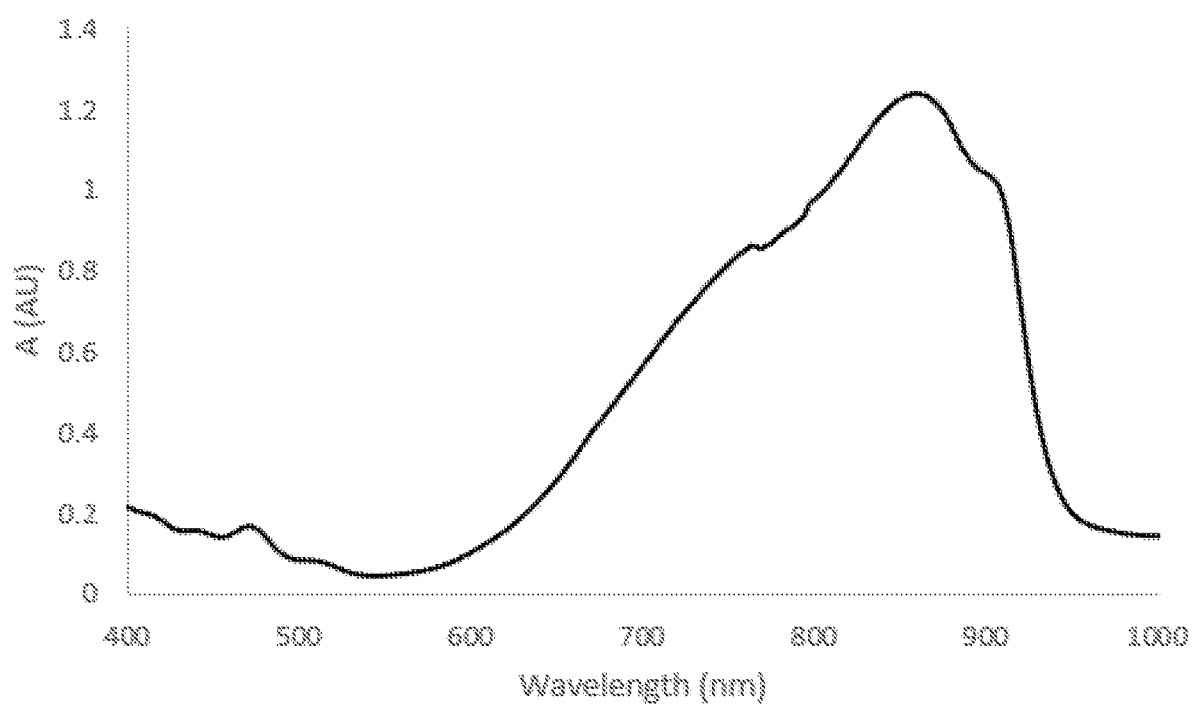
FIG. 1 illustrates an absorption spectrum of a ferroelectric nematic ($N_F$) composition in a 2 um parallel buffed sandwich cell, in accordance with some embodiments.

In one aspect, provided herein are ferroelectric nematic ($N_F$) compositions comprising a ferroelectric nematic host and one or more nonlinear optical compounds (chromophores). In certain embodiments, the nonlinear optical compound has a Formula of: D-B-A, wherein D is a donor moiety, B is a π-conjugated bridging moiety, and A is an acceptor moiety In some embodiments, the second order nonlinear optical (NLO) coefficient of the $N_F$ host is greater than 0.1, 0.2, 0.3, 0.4, 0.5, 0.6, 0.7, 0.8, 0.9, or 1 pm/V. In some embodiments, the NLO coefficient of the $N_F$ host is greater than 1 pm/V. In some embodiments, the NLO coefficient of the $N_F$ host is greater than 1, 2, 3, 4, 5, 6, 7, 8, 9, 10, 11, 12, 13, 14, 15, 16, 17, 18, 19, or 20 pm/V. In some embodiments, the NLO coefficient of the $N_F$ host is greater than 5, 10, 15, 20, 25, 30, 35, 40, 45, or 50 pm/V.

In some embodiments, the second order nonlinear optical (NLO) coefficient ($\chi^{(2)}$) of the nonlinear optical compound is higher than the NLO coefficient of the $N_F$ host. In some embodiments, the second order NLO coefficient ($\chi^{(2)}$) of the nonlinear optical compound is greater than 1, 2, 3, 4, 5, 10, 20, 30, 40, 50, 100, or 200 pm/V. In some embodiments, the second order NLO coefficient ($\chi^{(2)}$) of the nonlinear optical compound is greater than 1, 2, 3, 4, 5, 6, 7, 8, 9, or 10 pm/V. In some embodiments, the second order NLO coefficient ($\chi^{(2)}$) of the nonlinear optical compound is greater than 10, 20, 30, 40, 50, 60, 70, 80, 90, or 100 pm/V. In some embodiments, the $\chi^{(2)}$ is greater than 100 pm/V. In some embodiments, the $\chi^{(2)}$ is greater than 200 pm/V.

In some embodiments, the spontaneous polarization (Ps) of the ferroelectric nematic composition is greater than about 1, 2, 3, 4, 5, 6, 7, 8, 9, 10, 20, 30, 40, 50, 60, 70, 80, 90, or 100 µC/cm^2. In some embodiments, the spontaneous polarization (Ps) of the ferroelectric nematic composition is greater than about 1 µC/cm^2. In some embodiments, the spontaneous polarization (Ps) of the ferroelectric nematic composition is greater than about 10 µC/cm^2. In some embodiments, the spontaneous polarization (Ps) of the ferroelectric nematic composition is between about 1 to about 100 µC/cm^2, about 5 to about 100 µC/cm^2, about 10 to about 100 µC/cm^2, about 20 to about 100 µC/cm^2, about 30 to about 100 µC/cm^2, about 40 to about 100 µC/cm^2 or about 50 to about 100 µC/cm^2. In one embodiment, the spontaneous polarization (Ps) of the ferroelectric nematic composition is between about 1 to about 10 µC/cm^2. In one embodiment, the spontaneous polarization (Ps) of the ferroelectric nematic composition is between about 1 to about 9 µC/cm^2. In one embodiment, the spontaneous polarization (Ps) of the ferroelectric nematic composition is between about 1 to about 8 µC/cm^2. In one embodiment, the spontaneous polarization (Ps) of the ferroelectric nematic composition is between about 1 to about 7 µC/cm^2. In one embodiment, the spontaneous polarization (Ps) of the ferroelectric nematic composition is between about 1 to about 6 µC/cm^2. In one embodiment, the spontaneous polarization (Ps) of the ferroelectric nematic composition is between about 1 to about 5 µC/cm^2. In one embodiment, the spontaneous polarization (Ps) of the ferroelectric nematic composition is between about 1 to about 4 µC/cm^2. In one embodiment, the spontaneous polarization (Ps) of the ferroelectric nematic composition is between about 1 to about 3 µC/cm^2. In one embodiment, the spontaneous polarization (Ps) of the ferroelectric nematic composition is between about 3 to about 10 µC/cm^2. In one embodiment, the spontaneous polarization (Ps) of the ferroelectric nematic composition is between about 3 to about 20 µC/cm^2. In one embodiment, the spontaneous polarization (Ps) of the ferroelectric nematic composition is between about 3 to about 30 µC/cm^2.

In some embodiments, the $N_F$ host has a dielectric permittivity constant ε greater than about 1000, 2000, 3000, 4000, 5000, 6000, 7000, 8000, 9000, or 10000. In some embodiments, the $N_F$ host has a dielectric permittivity constant ε greater than about 1000, 2000, 3000, 4000, 5000, 6000, 7000, 8000, 9000, or 10000 at a frequency between 1 and 10 kHz. In some embodiments, the $N_F$ host has a dielectric permittivity constant ε greater than about 1000, 2000, 3000, 4000, 5000, 6000, 7000, 8000, 9000, or 10000 at any frequency between 1 and 10 kHz. In some embodiments, the $N_F$ host has a dielectric permittivity constant ε greater than about 1000, 2000, 3000, 4000, 5000, 6000, 7000, 8000, 9000, or 10000 at a frequency between 1 and 10 KHz. In some embodiments, the $N_F$ host has a dielectric permittivity constant ε greater than about 10000 at a frequency between 1 and 10 kHz. In some embodiments, the $N_F$ host has a dielectric permittivity constant ε greater than about 10000 at any frequency between 1 and 10 KHz.

In some embodiments, the $N_F$ host has a dipole moment (µ) greater than about 5 D, 6 D, 7 D, 8 D, 9 D, or 10 D. In some embodiments, the $N_F$ host has a dipole moment (µ) great than about 5 D. In some embodiments, the $N_F$ host has a dipole moment (µ) great than about 6 D. In some embodiments, the $N_F$ host has a dipole moment (µ) greater than about 7 D. In some embodiments, the $N_F$ host has a dipole moment (µ) greater than about 8 D. In some embodiments, the $N_F$ host has a dipole moment (µ) greater than about 9 D. In some embodiments, the $N_F$ host has a dipole moment (u) greater than about 10 D. In some embodiments, the $N_F$ host has a dipole moment (µ) greater than about 11 D, 12 D, 13 D, 14 D, 15 D, 16 D, 17 D, 18 D, 19 D, 20 D, 25 D, 30 D, 35 D, 40 D, or 45 D. In some embodiments, the $N_F$ host has a dipole moment (µ) between about 8 D and about 50 D. In some embodiments, the $N_F$ host has a dipole moment of between about 8 D and about 50 D. In some embodiments, the $N_F$ host has a dipole moment of between about 8 D and about 50 D. In some embodiments, the $N_F$ host has a dipole moment of between about 8 D and about 40 D. In some embodiments, the $N_F$ host has a dipole moment of between about 8 D and about 30 D. In some embodiments, the $N_F$ host has a dipole moment of between about 8 D and about 20 D. In some embodiments, the $N_F$ host has a dipole moment of between about 8 D and about 10 D. In some embodiments, the $N_F$ host has a dipole moment of between about 10 D and about 50 D. In some embodiments, the $N_F$ host has a dipole moment of between about 10 D and about 40 D. In some embodiments, the $N_F$ host has a dipole moment of between about 10 D and about 30 D. In some embodiments, the $N_F$ host has a dipole moment of between about 10 D and about 20 D. In some embodiments, the $N_F$ host has a dipole moment of between about 15 D and about 50 D. In some embodiments, the $N_F$ host has a dipole moment of between about 15 D and about 40 D. In some embodiments, the $N_F$ host has a dipole moment of between about 15 D and about 30 D. In some embodiments, the $N_F$ host has a dipole moment of between about 15 D and about 20 D. In some embodiments, the $N_F$ host has a dipole moment of between about 20 D and about 50 D. In some embodiments, the $N_F$ host has a dipole moment of between about 20 D and about 40 D. In some embodiments, the $N_F$ host has a dipole moment of between about 20 D and about 30 D.

In some embodiments, ferroelectric nematic ($N_F$) composition comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% w/w nonlinear optical compound(s). In some embodiments, ferroelectric nematic ($N_F$) composition comprises between about 1% to about 5% w/w nonlinear optical compound(s). In some embodiments, ferroelectric nematic ($N_F$) composition comprises between about 1% to about 10% w/w nonlinear optical compound(s). In some embodiments, ferroelectric nematic ($N_F$) composition comprises between about 1% to about 15% w/w nonlinear optical compound(s). In some embodiments, ferroelectric nematic ($N_F$) composition comprises between about 1% to about 20% w/w nonlinear optical compound(s). In some embodiments, ferroelectric nematic ($N_F$) composition comprises between about 1% to about 25% w/w nonlinear optical compound(s). In some embodiments, ferroelectric nematic ($N_F$) composition comprises between about 1% to about 30% w/w nonlinear optical compound(s). In some embodiments, ferroelectric nematic ($N_F$) composition comprises between about 1% to about 40% w/w nonlinear optical compound(s). In some embodiments, ferroelectric nematic ($N_F$) composition comprises between about 1% to about 50% w/w nonlinear optical compound(s).

By employing nonlinear optical compound(s), the nonlinear optical property of the $N_F$ host is improved without significant deterioration of the dielectric permissivity constant ε. A material containing such a nonlinear optical compound exhibiting a larger nonlinear optical effect can give a nonlinear optical element that can change the intensity and phase of light in response to even a weaker external field applied thereto. In some embodiments, the NLO coefficient of the $N_F$ composition is about 5%, 10%, 15%, 20%, 30%, 35%, 40%, 45%, 50%, 55%, 60%, 65%, 70%, 75%, 80%, 85%, 90%, 95%, or 100% greater than the NLO coefficient of the $N_F$ host. In some embodiments, the NLO coefficient of the $N_F$ composition is about 25%, 50%, 75%, 100%, 150%, or 200% greater than the NLO coefficient of the $N_F$ host.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. In some embodiments, about is within 10% of the stated number or numerical range. In some embodiments, about is within 5% of the stated number or numerical range. In some embodiments, about is within 1% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Alkyl" generally refers to a non-aromatic straight or branched hydrocarbon chain radical consisting solely of carbon and hydrogen atoms, partially or fully saturated, cyclic or acyclic, having from one to fifteen carbon atoms (e.g., $C_1$-$C_{18}$ alkyl). Unless otherwise state, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{12}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted.

"Alkylene" or "alkylene chain" refers to a straight or branched divalent hydrocarbon chain, having from one to twenty carbon atoms, linking the rest of the molecule to a radical group. In some embodiments, the alkylene is —$CH_2$—, —$CH_2CH_2$—, or —$CH_2CH_2CH_2$—. For non-limiting examples, the $C_1$ alkylene is —$CH_2$—; the $C_2$ alkylene is —$CH_2CH_2$—; the $C_3$ alkylene is —$CH_2CH_2CH_2$—, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$ heteroalkyl. Heteroalkyl may include nitriles, amides, esters, ethers, amines, thioethers, thioesters, carbamates, carbonates, polyethers, polyamines, and the like. Heteroalkyl may also include $C_{1-8}$ sulfane, such as propyl-$\lambda^1$-sulfane, butyl-$\lambda^1$-sulfane, pentyl-$\lambda^1$-sulfane, hexyl-$\lambda^1$-sulfane, heptyl-$\lambda^1$-sulfane, and the like.

The term "haloalkyl" refers to an alkyl group wherein at least one, and possibly more, hydrogen atoms have been replaced with a halogen. For example, haloalkyl includes alkyl derivatives, such as —$CH_2F$, —$CHF_2$, —$CF_3$, —$CF_2CF_3$, —$CF_2CF_2CF_3$, and the like. Haloalkyl is non-limiting in terms of number of halogens and carbons. Generally, haloalkyl refers to $C_1$-$C_{12}$ haloalkyl.

"Perfluorinated" refers to organofluorine compounds without any C—H bonds.

"Alkoxy" refers to a radical bonded through an oxygen atom of the formula-O-alkyl, where alkyl is as defined above. Unless stated otherwise specifically in the specification, an alkoxy group is optionally substituted, as defined above for an alkyl group.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene.

"Halo" or "halogen" refers to bromo, chloro, fluoro or iodo substituents. A "haloalkyl" refers to an alkyl radical, as described herein, that is substituted with one or more halo radical, such as described above.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl).

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, a substituted group provided herein (e.g., substituted alkyl) is substituted by one or more substituent, each substituent being independently selected from the group consisting of halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2), where each R$^a$ is independently hydrogen, alkyl (e.g., optionally substituted with halogen, hydroxy, methoxy, or trifluoromethyl), fluoroalkyl, carbocyclyl (e.g., optionally substituted with halogen, hydroxy, methoxy, or trifluoromethyl), carbocyclylalkyl (e.g., optionally substituted with halogen, hydroxy, methoxy, or trifluoromethyl), aryl (e.g., optionally substituted with halogen, hydroxy, methoxy, or trifluoromethyl), aralkyl (e.g., optionally substituted with halogen, hydroxy, methoxy, or trifluoromethyl), heterocyclyl (e.g., optionally substituted with halogen, hydroxy, methoxy, or trifluoromethyl), heterocyclylalkyl (e.g., optionally substituted with halogen, hydroxy, methoxy, or trifluoromethyl), heteroaryl (e.g., optionally substituted with halogen, hydroxy, methoxy, or trifluoromethyl), or heteroarylalkyl (e.g., optionally substituted with halogen, hydroxy, methoxy, or trifluoromethyl).

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Ferroelectric Nematic (N$_F$) Host

In some embodiments, the N$_F$ host comprises one or more compounds of Formula (I):

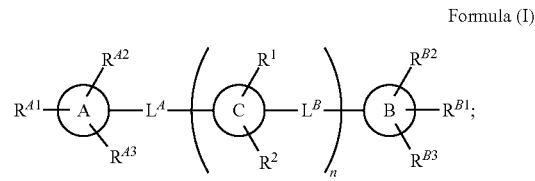

Formula (I)

wherein
ring A, ring B, and each ring C are independently an aryl;
L$^A$ and each L$^B$ are independently a bond, —N=N—, or

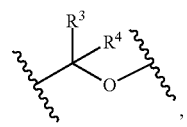

wherein R$^3$ and R$^4$ are each fluoro or R$^3$ and R$^4$ form an oxo;
R$^1$ and R$^2$ are each independently hydrogen, fluoro, or C$_{1-6}$ alkoxy;
R$^{A1}$ is hydrogen, C$_{1-6}$ alkyl, C$_{1-6}$ alkoxy, C$_{1-6}$ heteroalkyl, or

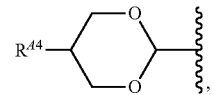

wherein R$^{A4}$ is C$_{1-6}$ alkyl;
R$^{A2}$ and R$^{A3}$ are each independently hydrogen, fluoro, or —OR, wherein R is C$_{1-6}$ alkyl optionally substituted with a C$_{1-6}$ alkoxy;

$R^{B1}$ is fluoro, —NO$_2$, or —CN;

$R^{B2}$ and $R^{B3}$ are each independently hydrogen, fluoro, or methoxy; and n is an integer of 1 to 8;

provided at least one of $L^A$ and $L^B$ is not a bond.

In some embodiments, ring A, ring B, and each ring C are independently phenyl or naphthyl. In some embodiments, ring A and ring B are phenyl and each ring C is naphthyl. In some embodiments, ring A and ring B are naphthyl and each ring C is phenyl. In some embodiments, ring A, ring B, and each ring C are phenyl. In some embodiments, ring A, ring B, and each ring C are naphthyl.

In some embodiments, the compound of Formula (I) has a structure of Formula (Ia):

Formula (Ia)

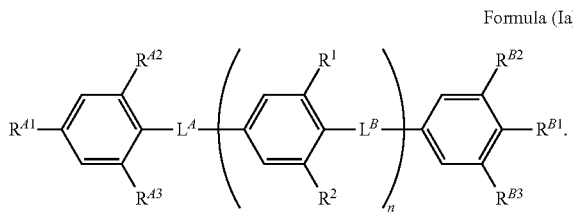

In some embodiments, the compound of Formula (I) has a structure of Formula (Ib):

Formula (Ib)

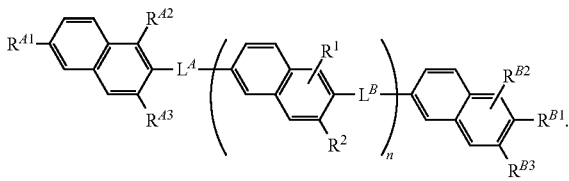

In some embodiments, the compound of Formula (I) has a structure of Formula (Ib'):

Formula (Ib')

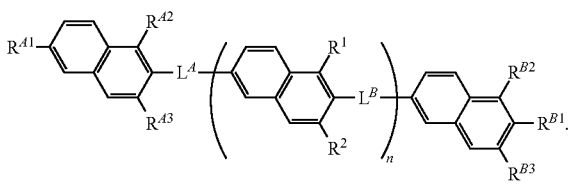

In some embodiments, $L^A$ and each $L^B$ are

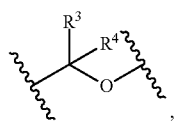

wherein $R^3$ and $R^4$ are each fluoro or $R^3$ and $R^4$ form an oxo. In some embodiments, $L^A$ and each $L^B$ are

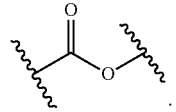 [SMILES: *OC(*)=O]

In some embodiments, $L^A$ is a bond and each $L^B$ is

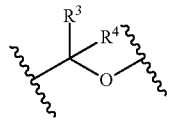

In some embodiments, $L^A$ is

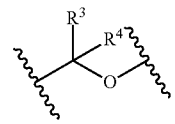

and each $L^B$ is a bond. In some embodiments, $L^A$ is a bond and $L^B$ is —CF$_2$O—. In some embodiments, $L^A$ is —CF$_2$O— and each $L^B$ is a bond. In some embodiments, $L^A$ and each $L^B$ are —CF$_2$O—. In some embodiments, $L^A$ is

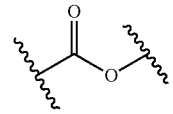 [SMILES: *OC(*)=O]

and each $L^B$ is a bond. In some embodiments, $L^A$ is a bond and $L^B$ is

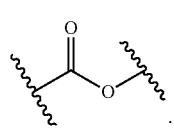 [SMILES: *OC(*)=O]

In some embodiments, $L^A$ is

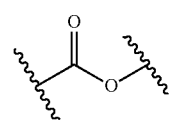 [SMILES: *OC(*)=O]

and each $L^B$ is —N=N—. In some embodiments, $L^A$ is —N=N— and each $L^B$ is

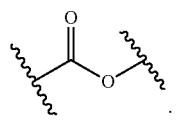 [SMILES: *OC(*)=O]

In some embodiments, $L^A$ and each $L^B$ are —N=N—.

In some embodiments, $R^1$ and $R^2$ are each hydrogen. In some embodiments, $R^1$ and $R^2$ are each fluoro. In some embodiments, $R^1$ is hydrogen and $R^2$ is $C_{1-6}$ alkoxy. In some embodiments, $R^1$ is hydrogen and $R^2$ is methoxy, ethoxy, n-propoxy, or n-butoxy. In some embodiments, $R^1$ is hydrogen and $R^2$ is fluoro.

In some embodiments,

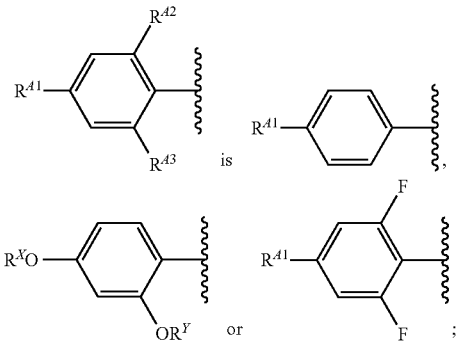

$R^{A1}$ is $C_{1-6}$ alkyl or

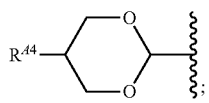

wherein $R^X$ is $C_{1-6}$ alkyl and $R^Y$ is $C_{1-6}$ alkyl optionally substituted with methoxy.

In some embodiments,

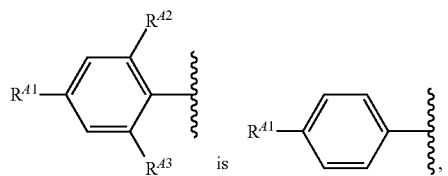

wherein $R^{A1}$ is methoxy. In some embodiments,

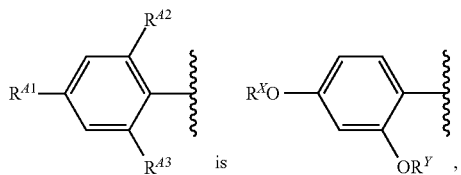

and $R^X$ is methyl or ethyl, and $R^Y$ is methyl, ethyl, n-propyl, or methoxyethyl. In some embodiments,

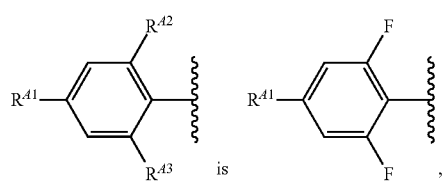

$R^{A1}$ is $C_{1-6}$ alkyl,

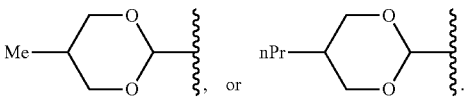

In some embodiments, $R^{A1}$ is $C_{1-6}$ alkyl. In some embodiments, $R^{A1}$ is methyl, ethyl, n-propyl, n-butyl, n-pentyl, or n-hexyl. In some embodiments, $R^{A1}$ is n-propyl. In some embodiments, $R^{A1}$ is

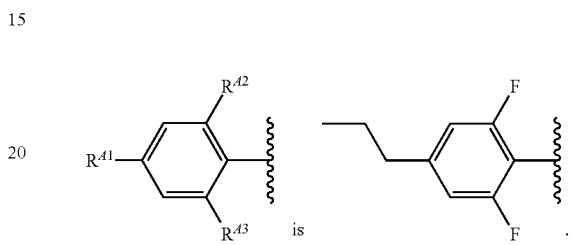

In some embodiments, $R^{A1}$ is

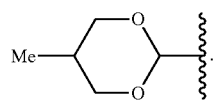

In some embodiments, $R^{A1}$ is

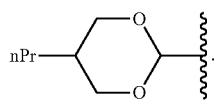

In certain embodiments,

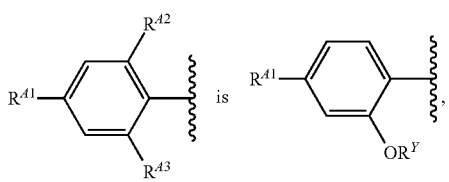

$R^{A1}$ is hydrogen, $C_{1-6}$ alkyl, $C_{1-6}$ alkoxy, $C_{1-6}$ heteroalkyl, or

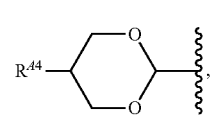

and $R^{A4}$ is $C_{1-6}$ alkyl, $R^Y$ is $C_{1-6}$ alkyl optionally substituted with a $C_{1-6}$ alkoxy.

In some embodiments,

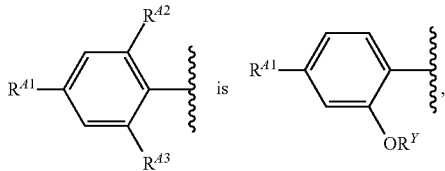

and $R^{A1}$ is $C_{1-6}$ alkyl, $C_{1-6}$ alkoxy, or $C_{1-6}$ heteroalkyl. In some embodiments, $R^{A1}$ is $C_{1-6}$ alkyl, —O—($C_{1-6}$ alkyl), or —N($C_{1-6}$ alkyl) ($C_{1-6}$ alkyl). In some embodiments, $R^{A1}$ is —N($C_{1-6}$ alkyl) ($C_{1-6}$ alkyl). In some embodiments, $R^{A1}$ is -N(Me)$_2$. In some embodiments, $R^{A1}$ is —N(Et)$_2$.

In some embodiments,

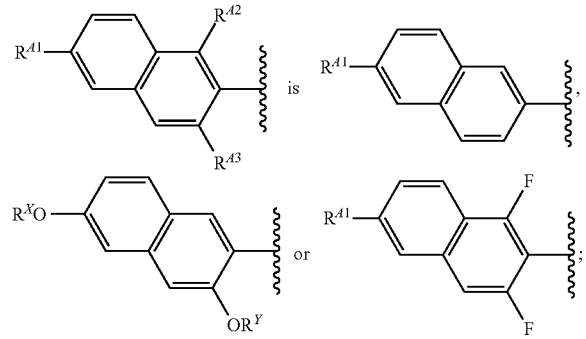

$R^{A1}$ is $C_{1-6}$ alkyl or

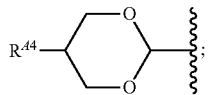

wherein $R^X$ is $C_{1-6}$ alkyl and $R^Y$ is $C_{1-6}$ alkyl optionally substituted with methoxy.

In some embodiments,

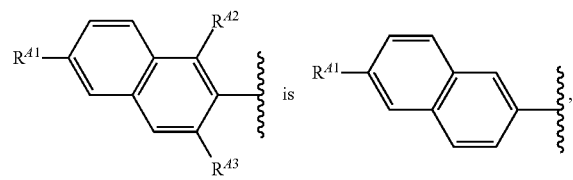

wherein $R^{A1}$ is methoxy. In some embodiments,

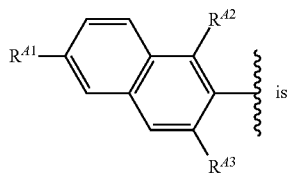

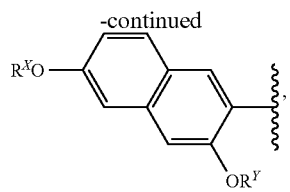

and $R^X$ is methyl or ethyl, and $R^Y$ is methyl, ethyl, n-propyl, or methoxyethyl. In some embodiments,

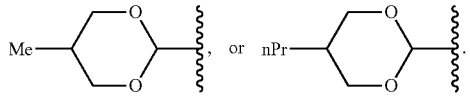

$R^{A1}$ is $C_{1-6}$ alkyl,

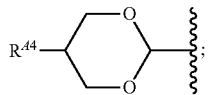

In some embodiments, $R^{A1}$ is $C_{1-6}$ alkyl. In some embodiments, $R^{A1}$ is methyl, ethyl, n-propyl, n-butyl, n-pentyl, or n-hexyl. In some embodiments, $R^{A1}$ is n-propyl. In some embodiments,

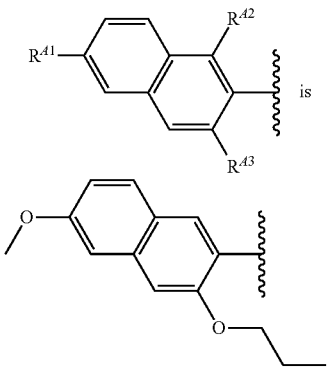

In some embodiments,

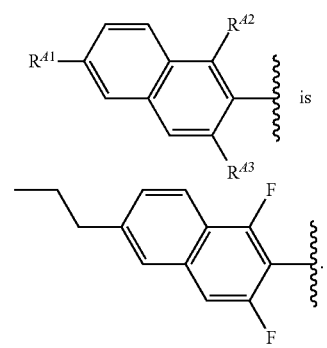

In some embodiments, $R^{A1}$ is

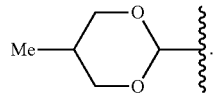

In some embodiments, $R^{A1}$ is

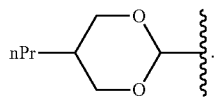

In some embodiments,

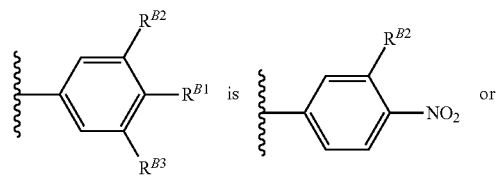

wherein $R^{B2}$ is hydrogen or fluoro, and $R^{B1}$ is —CN or fluoro. In some embodiments,

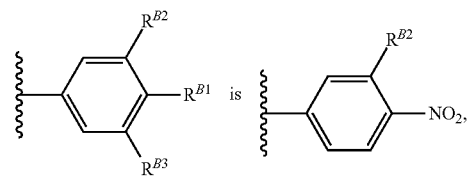

wherein $R^{B2}$ is hydrogen or fluoro. In some embodiments, $R^{B2}$ is hydrogen. In some embodiments, $R^{B2}$ is fluoro. In some embodiments,

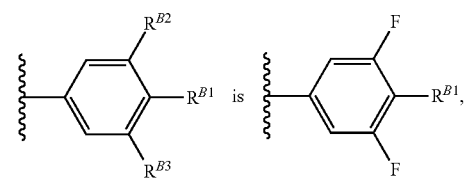

wherein $R^{B1}$ is —CN or fluoro. In some embodiments, $R^{B1}$ is —CN. In some embodiments, $R^{B1}$ is fluoro.

In some embodiments,

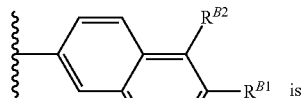

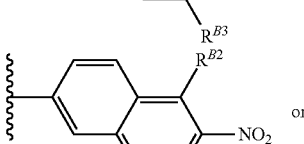

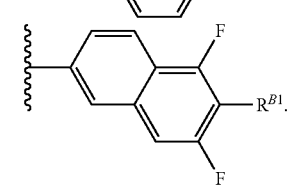

In some embodiments,

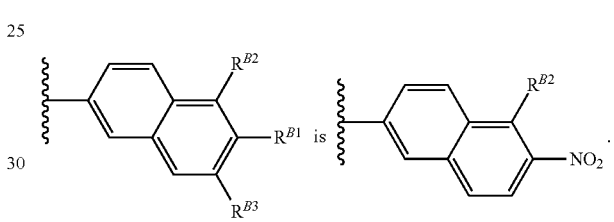

In some embodiments,

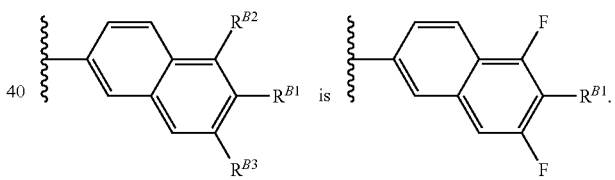

In one embodiment,

In another embodiment,

In some embodiments, $R^1$ and $R^2$ are each independently hydrogen or $C_{1-6}$ alkoxy. In some embodiments, $R^1$ and $R^2$ are each independently hydrogen, methoxy, ethoxy, n-propoxy, i-propoxy, n-butoxy, i-butoxy, n-pentoxy, or i-pentoxy. In some embodiments, $R^1$ and $R^2$ are hydrogen. In some embodiments, $R^1$ is hydrogen, and $R^2$ is methoxy, ethoxy, n-propoxy, i-propoxy, n-butoxy, i-butoxy, n-pentoxy, or i-pentoxy. In some embodiments, $R^1$ is hydrogen, and $R^2$ is methoxy, ethoxy, or n-propoxy. In one embodiment, $R^1$ is hydrogen, and $R^2$ is methoxy. In another embodiment, $R^1$ is hydrogen, and $R^2$ is ethoxy. In another embodiment, $R^1$ is hydrogen, and $R^2$ is n-propoxy.

In some embodiments, $R^1$ and $R^2$ are fluoro. In some embodiments, $R^1$ is hydrogen and $R^2$ is fluoro.

In some embodiments,

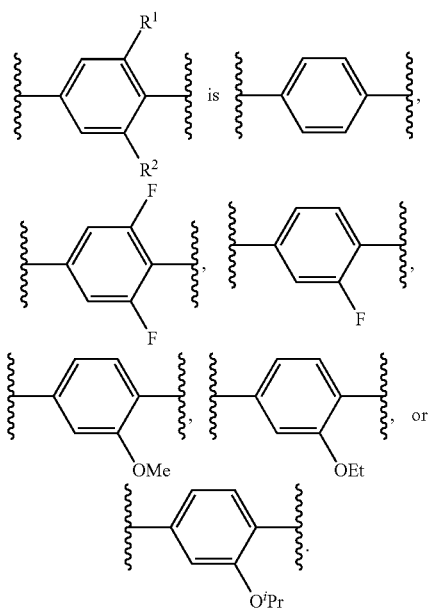

In some embodiments,

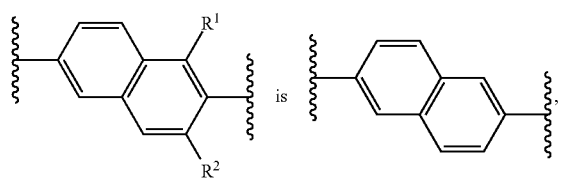

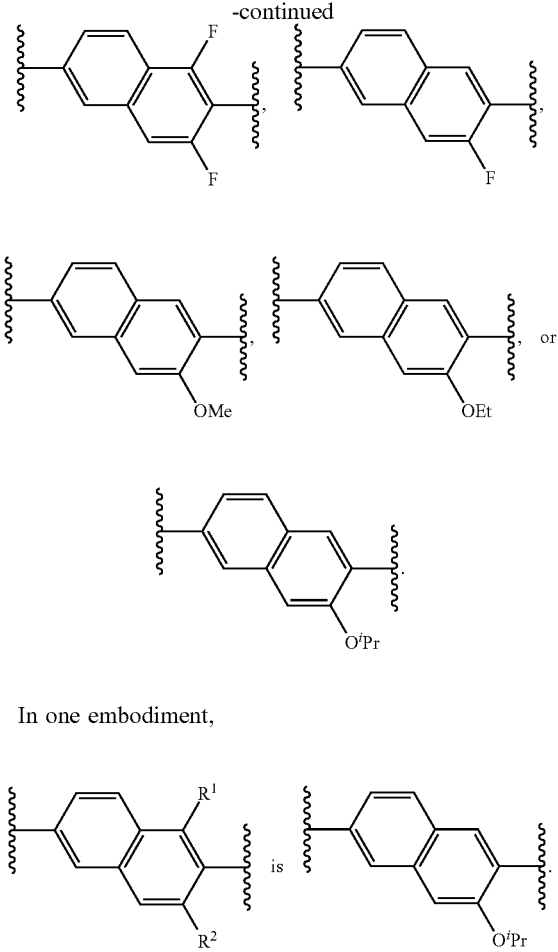

In one embodiment,

In some embodiments, n is an integer of 1 to 8. In some embodiments, n is an integer of 1 to 7. In some embodiments, n is an integer of 1 to 6. In some embodiments, n is an integer of 1 to 5. In some embodiments, n is an integer of 1 to 4. In some embodiments, n is an integer of 1 to 3. In some embodiments, n is an integer of 1 to 2. In some embodiments, n is an integer of 1, 2, 3, 4, 5, 6, 7, or 8. In one embodiment, n is 1. In another embodiment, n is 2. In yet another embodiment, n is 3. In yet another embodiment, n is 4. In yet another embodiment, n is 5. In yet another embodiment, n is 6. In yet another embodiment, n is 7.

In some embodiments, the compound of Formula (I) is selected from the group consisting of:

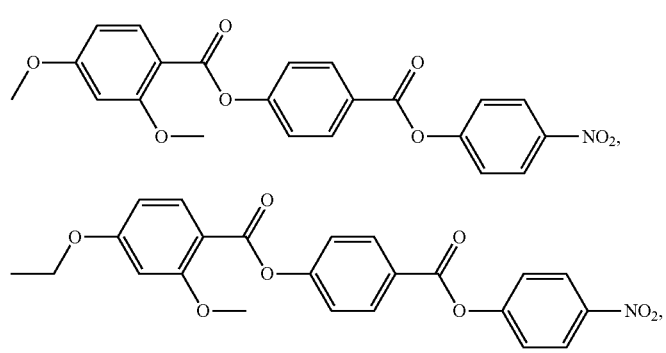

-continued
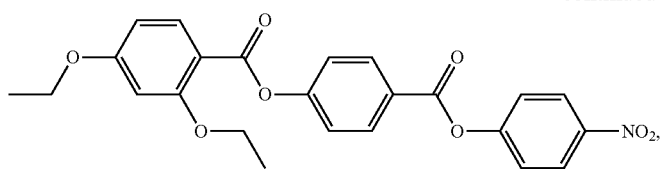
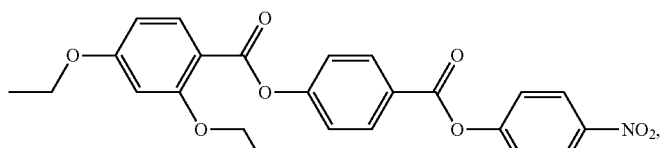
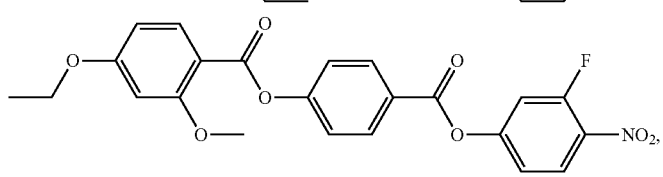
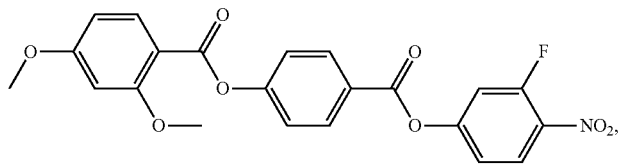
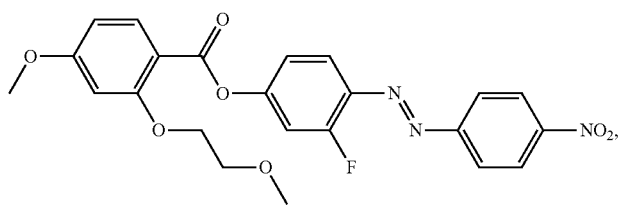
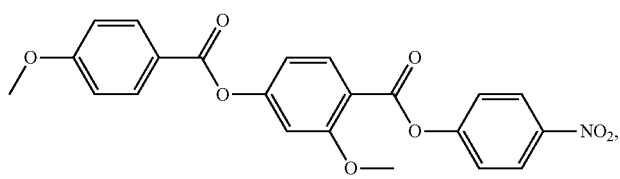
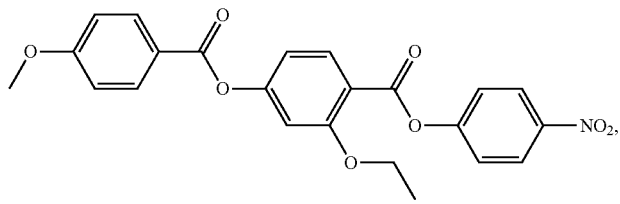
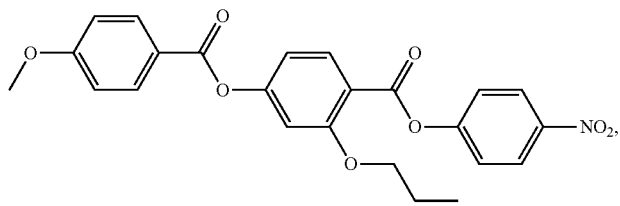
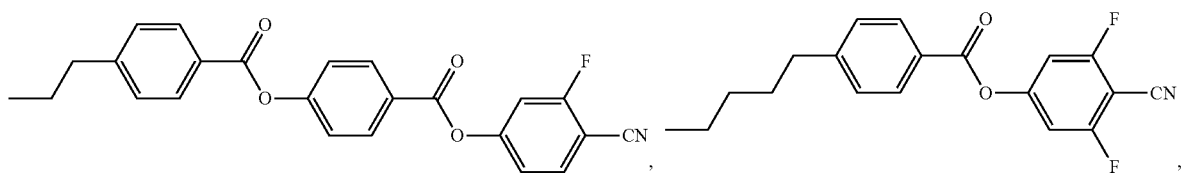

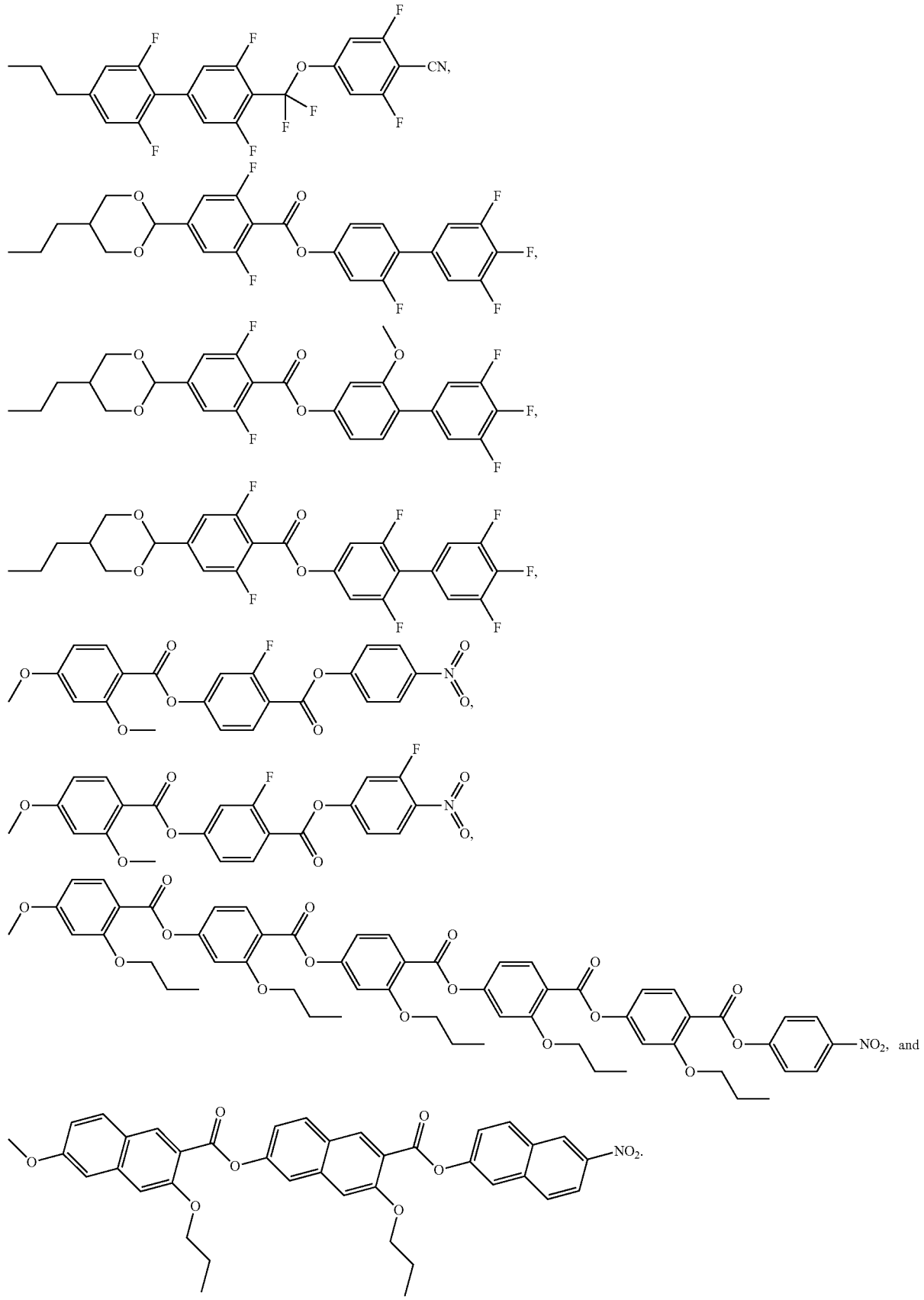

In some embodiments, the $N_F$ host comprising a structure of:

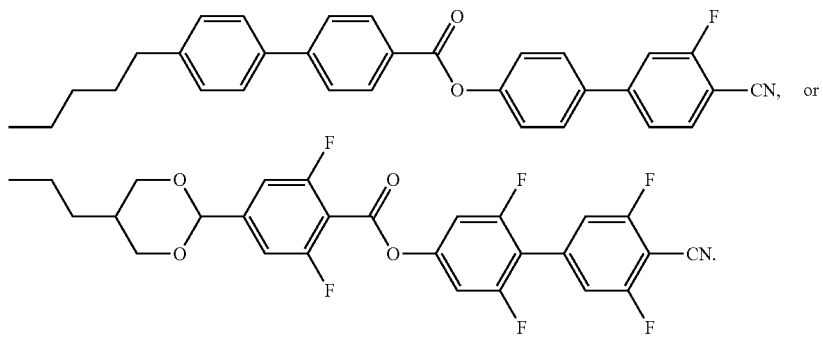

In some embodiments, the $N_F$ host is a polymer.

In some embodiments, the $N_F$ host is a polymer having a recurring unit of Formula (II):

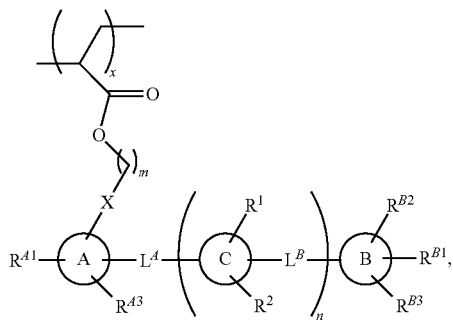

wherein
ring A, ring B, and each ring C are independently an aryl;
$L^A$ and each $L^B$ are independently a bond, —N=N—, or

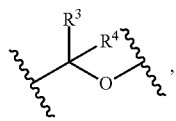

wherein $R^3$ and $R^4$ are each fluoro or $R^3$ and $R^4$ form an oxo;
$R^1$ and $R^2$ are each independently hydrogen, fluoro, or $C_{1-4}$ alkoxy;
$R^{A1}$ is hydrogen, $C_{1-6}$ alkyl, $C_{1-6}$ alkoxy, $C_{1-6}$ heteroalkyl, or

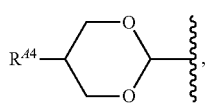

wherein $R^{A4}$ is $C_{1-6}$ alkyl;
$R^{A2}$ and $R^{A3}$ are each independently hydrogen, fluoro, or —OR, wherein R is $C_{1-6}$ alkyl optionally substituted with a $C_{1-6}$ alkoxy;
$R^{B1}$ is fluoro, —$NO_2$, or —CN;
$R^{B2}$ and $R^{B3}$ are each independently hydrogen, fluoro, or methoxy;
n is an integer of 1 to 8;
x is an integer of 1 to 100;
at least one of $L^A$ and $L^B$ is not a bond; and
X is O or $NR^N$, wherein $R^N$ is hydrogen, —OH, benzyl, or $C_{1-6}$ alkyl; and
m is an integer of 1 to 30.

In some embodiments, X is O or $NR^N$, wherein $R^N$ is hydrogen, —OH, benzyl, or $C_{1-6}$ alkyl. In some embodiments, X is O. In some embodiments, X is O or $NR^N$. In some embodiments, $R^N$ is hydrogen, —OH, benzyl, or $C_{1-6}$ alkyl. In some embodiments, $R^N$ is hydrogen, methyl or ethyl. In some embodiments, $R^N$ is hydrogen. In some embodiments, $R^N$ is methyl. In some embodiments, X is O, NH, or NMe. In some embodiments, X is O or NH. In some embodiments, X is NH.

In some embodiments, m is an integer of 1 to 30. In some embodiments, m is an integer of 1 to 25. In some embodiments, m is an integer of 1 to 20. In some embodiments, m is an integer of 1 to 15. In some embodiments, m is an integer of 1 to 10. In some embodiments, m is an integer of 1 to 9. In some embodiments, m is an integer of 1 to 8. In some embodiments, m is an integer of 1 to 7. In some embodiments, m is an integer of 1 to 6. In some embodiments, m is an integer of 1 to 6. In some embodiments, m is an integer of 1 to 5. In some embodiments, m is an integer of 1 to 4. In some embodiments, m is an integer of 1 to 3. In some embodiments, m is 1 or 2. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9.

In some embodiments, n is an integer of 1 to 8. In some embodiments, n is an integer of 1 to 7. In some embodiments, n is an integer of 1 to 6. In some embodiments, n is an integer of 1 to 5. In some embodiments, n is an integer of 1 to 4. In some embodiments, n is an integer of 1 to 3. In some embodiments, n is an integer of 1 to 2. In some embodiments, n is an integer of 1, 2, 3, 4, 5, 6, 7, or 8. In one embodiment, n is 1. In another embodiment, n is 2. In yet another embodiment, n is 3. In yet another embodiment, n is 4. In yet another embodiment, n is 5. In yet another embodiment, n is 6. In yet another embodiment, n is 7.

In some embodiments, m is 6 and X is O.

In some embodiments, x is an integer of 1 to 100. In some embodiments, x is an integer of 1 to 90. In some embodiments, x is an integer of 1 to 80. In some embodiments, x is an integer of 1 to 70. In some embodiments, x is an integer of 1 to 60. In some embodiments, x is an integer of 1 to 50. In some embodiments, x is an integer of 1 to 40. In some embodiments, x is an integer of 1 to 30. In some embodiments, x is an integer of 1 to 20. In some embodiments, x is an integer of 1 to 10. In some embodiments, x is an integer of 1 to 9. In some embodiments, x is an integer of 1 to 8. In some embodiments, x is an integer of 1 to 7. In some embodiments, x is an integer of 1 to 6. In some embodiments, x is an integer of 1 to 5. In some embodiments, x is an integer of 1 to 4. In some embodiments, x is an integer of 1 to 3. In some embodiments, x is an integer of 1 to 2.

In some embodiments, the compound of Formula (II) is a compound having a Formula (IIa):

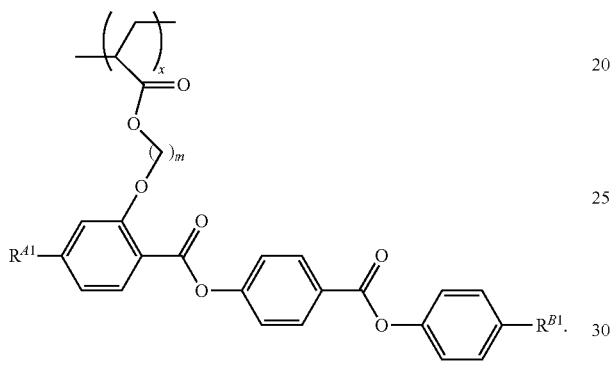

Formula (IIa)

In some embodiments, the compound of Formula (II) is:

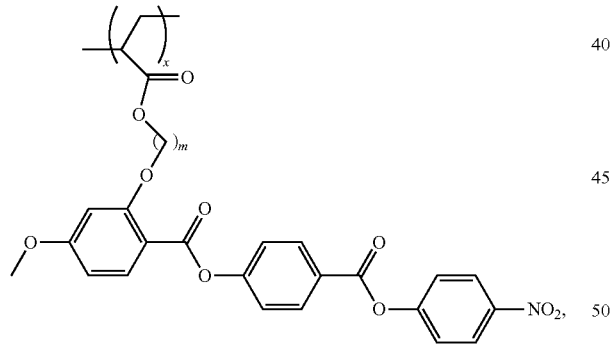

wherein m is 6.

In some embodiments, the compound of Formula (I) or Formula (II) said molecules having spontaneously formed a ferroelectric polarization density. In some embodiments, the ferroelectric polarization density of the compound of Formula (I) or Formula (II) in the $N_F$ host has a nonzero local unidirectional average orientation of dipoles.

Nonlinear Optical Compound Dopant

In some embodiments, the nonlinear optical dopant having a Formula of: D-B-A, wherein D is a donor moiety, B is a π-conjugated bridging moiety, and A is an acceptor moiety.

In some embodiments, in the nonlinear optical compound of Formula D-B-A, D is

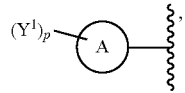

wherein Ring A is an aryl or heteroaryl ring,
each $Y^1$ is independently -OH, fluoro, $NR^5R^6$ or $C_{1-6}$ alkoxy, wherein $R^5$ and $R^6$ are each independently hydrogen or $C_{1-6}$ alkyl; p is an integer of 0 to 5.

In some embodiments, Ring A is an aryl. In some embodiments, Ring A is phenyl. In some embodiments, Ring A is a heteraryl. In some embodiments, Ring A is pyrrole.

In some embodiments, p is 0 to 4. In some embodiments, p is 0 to 3. In some embodiments, p is 0 to 2. In some embodiments, p is 0 or 1.

In some embodiments, when Ring A is phenyl, p is 1. In some embodiments, when Ring A is phenyl, p is 2. In some embodiments, when Ring A is phenyl, p is 3. In some embodiments, when Ring A is pyrrole, p is 0.

In some embodiments, D is selected from:

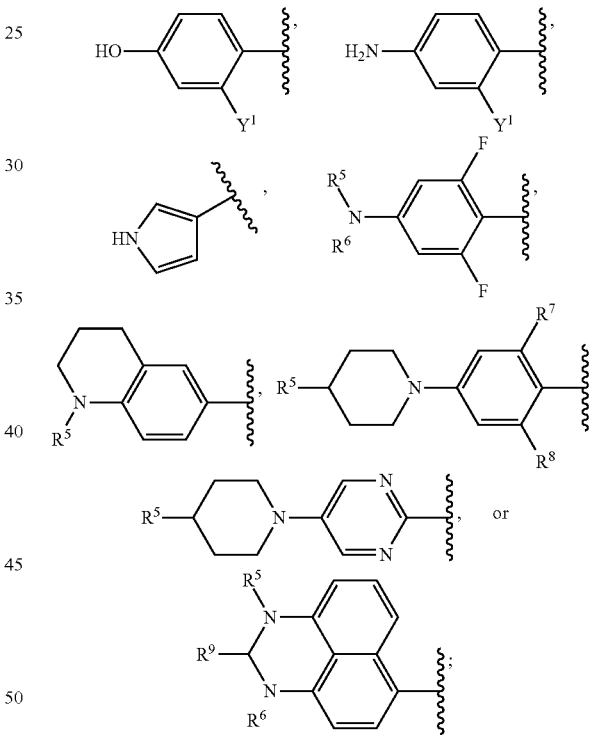

wherein $R^5$, $R^6$ and $R^9$ are each independently hydrogen or $C_{1-6}$ alkyl, and $R^7$ and $R^8$ are each independently hydrogen or $C_{1-6}$ alkoxy.

In some embodiments, D is

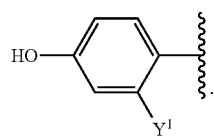

In some embodiments, $Y^1$ is OH, fluoro, $NR^5R^6$ or $C_{1-6}$ alkoxy. In some embodiments, $Y^1$ is OH. In some embodiments, $Y^1$ is fluoro. In some embodiments, $Y^1$ is $NR^5R^6$. In one embodiment, $Y^1$ $NH_2$. In some embodiments, $Y^1$ is $C_{1-6}$ alkoxy. In one embodiment, $Y^1$ methoxy, ethoxy, n-propoxy, or n-butoxy. In one embodiment, $Y^1$ is methoxy.

In some embodiments, D is

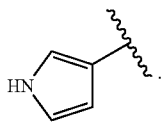

In some embodiments, D is

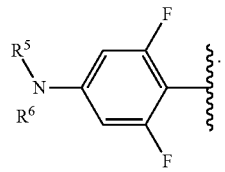

In one embodiment, $NR^5R^6$ is $N(CH_3)_2$. In another embodiment, $NR^5R^6$ is $NH_2$.

In some embodiments, D is

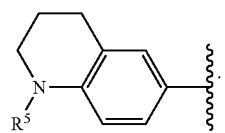

In some embodiments, D is

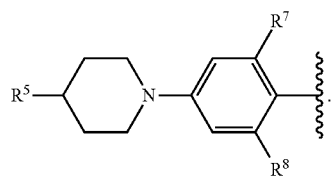

In some embodiments, D is

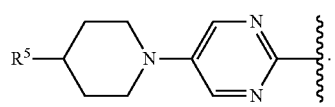

In some embodiments, D is

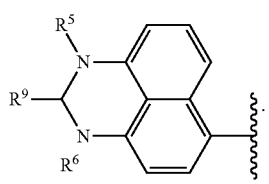

In some embodiments, in the nonlinear optical compound of Formula D-B-A, D is:

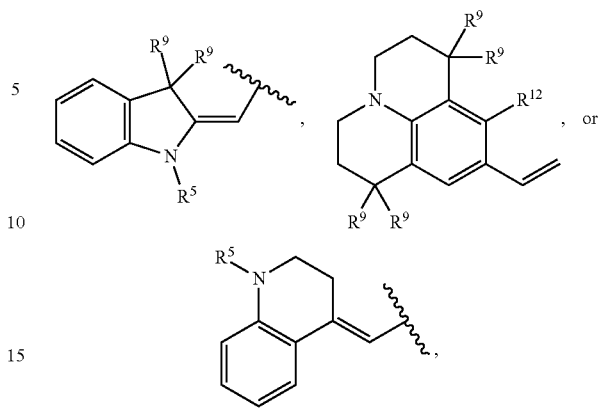

wherein $R^5$, $R^6$ and $R^9$ are each independently hydrogen or $C_{1-6}$ alkyl, and $R^{12}$ is hydrogen, $C_{1-10}$ alkyl, $C_{1-10}$ heteroalkyl, —O—$C_{1-10}$ alkyl, —O—$C_{1-10}$ heteroalkyl, —O—$C_{0-9}$ alkylene-$C_{6-10}$ aryl, —O—$C_{0-9}$ alkylene-$C_{1-10}$ heteroaryl, or —$NR^5R^6$.

In some embodiments, in the nonlinear optical compound of Formula D-B-A, D is:

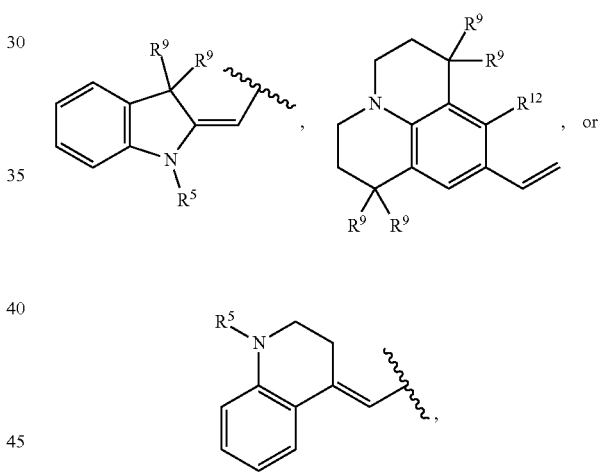

wherein $R^5$, $R^6$ and $R^9$ are each independently hydrogen, methyl, or ethyl, and $R^{12}$ is hydrogen, $C_{1-6}$ alkyl, $C_{1-6}$ heteroalkyl, —O—$C_{1-6}$ alkyl, —O—$C_{1-6}$ heteroalkyl, —O—$C_{0-6}$ alkylene-$C_{6-10}$ aryl, or —O—$C_{0-6}$ alkylene-$C_{1-10}$ heteroaryl.

In some embodiments, in the nonlinear optical compound of Formula D-B-A, D is:

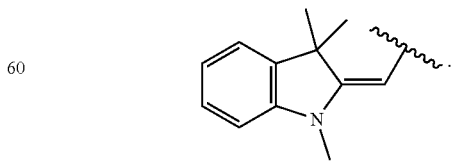

In some embodiments, in the nonlinear optical compound of Formula D-B-A, B is selected from:

a bond,

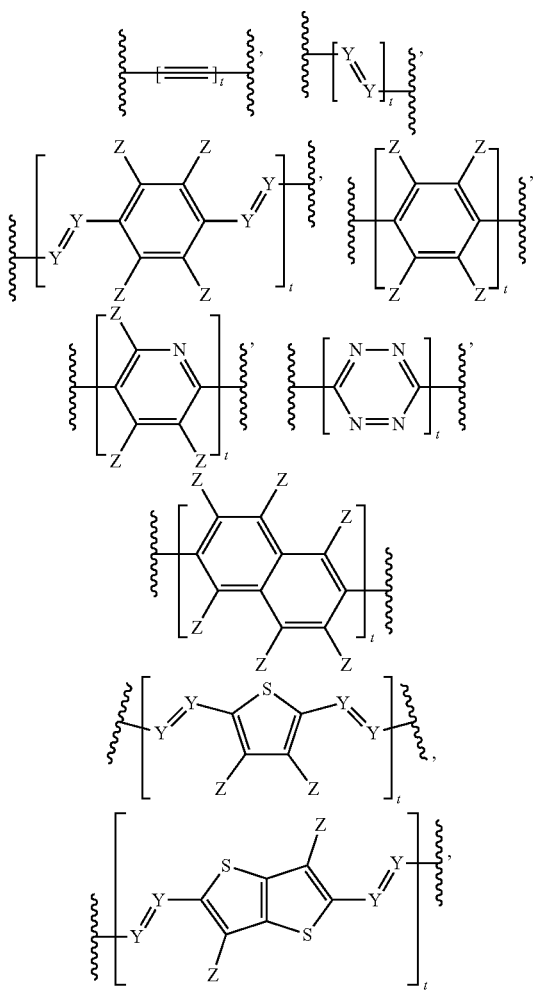

and a combination thereof; wherein each Y is independently —N= or —CH—, each Z is independently hydrogen, fluoro, chloro, or $C_{1-6}$ alkoxy, and t is an integer of 1 to 4.

In some embodiments, B is a bond. In some embodiments, B is

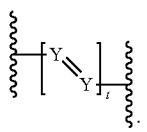

In some embodiments, B is

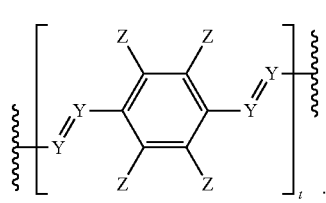

In some embodiments, B is

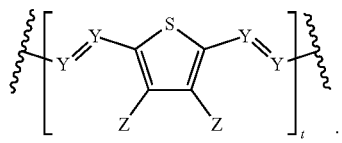

In some embodiments, B is

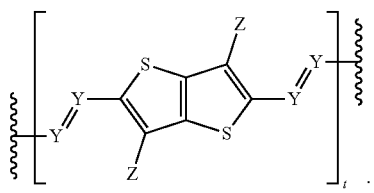

In some embodiments, B is

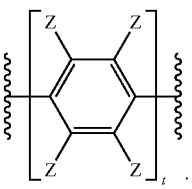

In some embodiments, B is

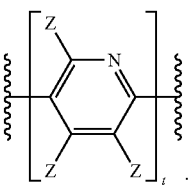

In some embodiments, B is

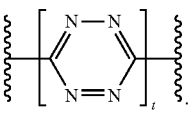

In some embodiments, B is

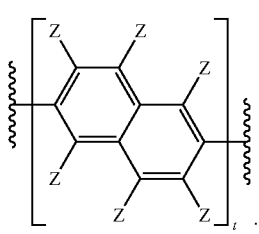

In some embodiments, B comprises two or more of

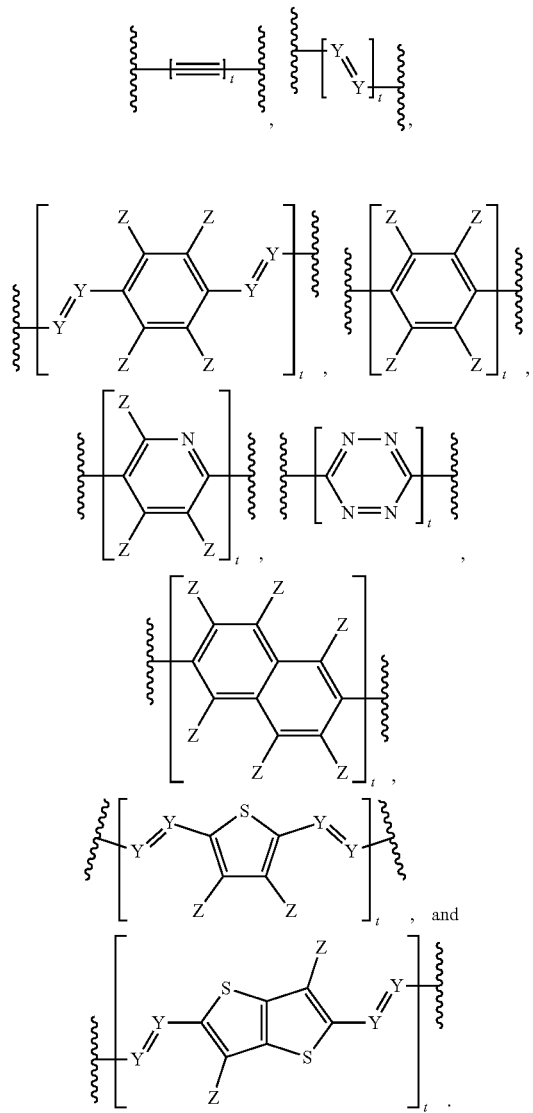

In some embodiments, in the nonlinear optical compound of Formula D-B-A, B is:

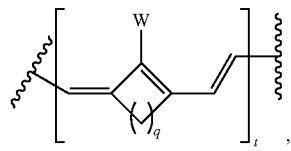

wherein W is hydrogen, fluoro, chloro, $C_{1-8}$ alkyl, $C_{1-8}$ alkoxy, $C_{1-8}$ heteroalkyl, or $C_{1-8}$ haloalkyl, q is an integer of 0 to 5, and t is an integer of 1 to 4.

In some embodiments, q is 1, 2, 3, or 4. In some embodiments, q is 1. In some embodiments, q is 2. In some embodiments, q is 3. In some embodiments, q is 4.

In some embodiments, in the nonlinear optical compound of Formula D-B-A Bis.

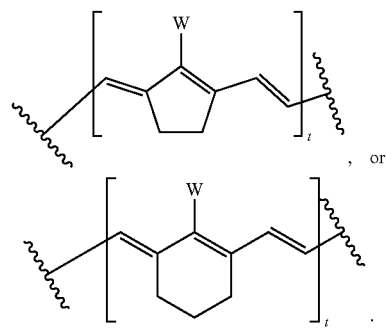

, or

In some embodiments, each Y is —N═. In some embodiments, each Y is —CH═.

In some embodiments, each Z is fluoro. In some embodiments, each Z is hydrogen.

In some embodiments, in the nonlinear optical compound of Formula D-B-A, W is hydrogen, fluoro, chloro, $C_{1-8}$ alkyl, $C_{1-8}$ alkoxy, $C_{1-8}$ heteroalkyl, or $C_{1-8}$ haloalkyl. In some embodiments, W is hydrogen. In some embodiments, W is fluoro. In some embodiments, W is chloro. In some embodiments, W is $C_{1-8}$ alkyl. In some embodiments, W is $C_{1-8}$ alkoxy. In some embodiments, W is $C_{1-8}$ heteroalkyl. In some embodiments, W is $C_{1-8}$ haloalkyl.

In some embodiments, W is $C_{1-8}$ alkyl, $C_{1-8}$ heteroalkyl, or $C_{1-8}$ haloalkyl. In some embodiments, W is $C_{1-8}$ heteroalkyl. In some embodiments, W is —S—($C_{1-8}$ alkyl), —O—($C_{1-8}$ alkyl), or —N($C_{1-8}$ alkyl)($C_{1-8}$ alkyl). In some embodiments, W is —S-(butyl), —S-(pentyl), -or S-(hexyl).

In some embodiments, W is $C_{1-8}$ sulfanyl. In some embodiments, W is propyl-$\lambda^1$-sulfane. In some embodiments, W is butyl-$\lambda^1$-sulfane. In some embodiments, W is pentyl-$\lambda^1$-sulfane. In some embodiments, W is hexyl-$\lambda^1$-sulfane. In some embodiments, W is heptyl-$\lambda^1$-sulfane.

In some embodiments, t is an integer of 1 to 4. In some embodiments, t is an integer of 1 to 3. In some embodiments, t is an integer of 1 to 2. In one embodiment, t is 1. In another embodiment, t is 2. In another embodiment, t is 3.

In some embodiments, B is selected from:
a bond,

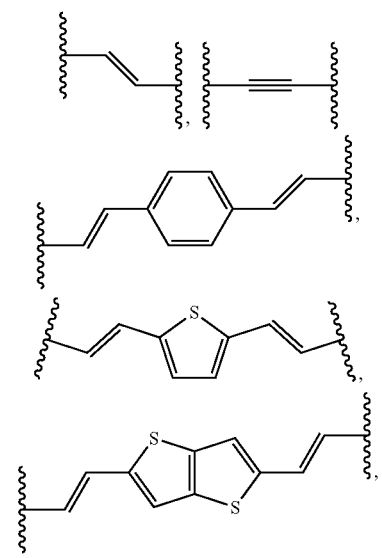

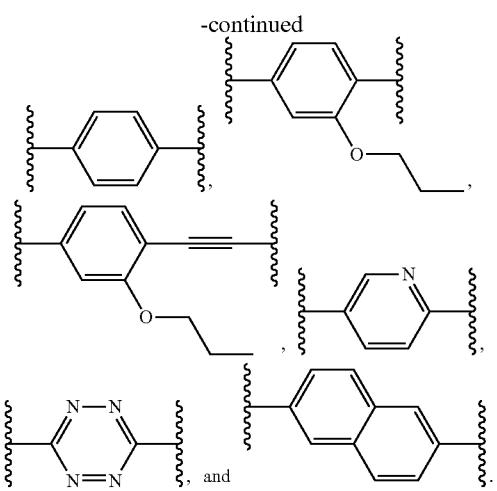

In some embodiments, B is:

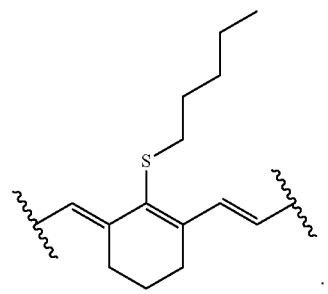 [SMILES: */C=C/C1=C(SCCCCC)C(=C/*)/CCC1]

In some embodiments, B is selected from:

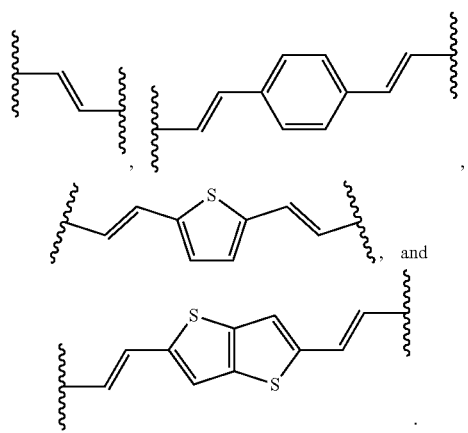

In some embodiments, wherein in the nonlinear optical compound of Formula D-B-A, A is selected from:

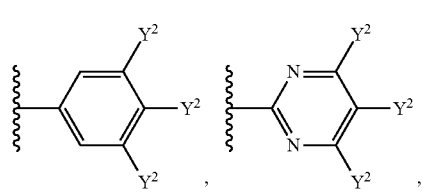

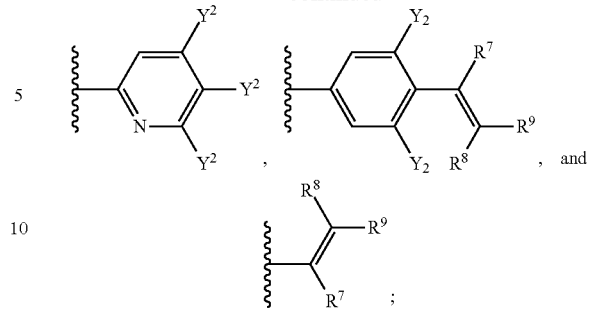

wherein each $Y^2$ is hydrogen, fluoro, chloro, —$NO_2$, —CN, —NCS, $SO_2CH_3$, or $SO_2CF_3$; $R^7$, $R^8$, and $R^9$ are each independently hydrogen or —CN, and at least one of $R^7$, $R^8$, and $R^9$ is —CN.

In some embodiments, wherein in the nonlinear optical compound of Formula D-B-A, A is:

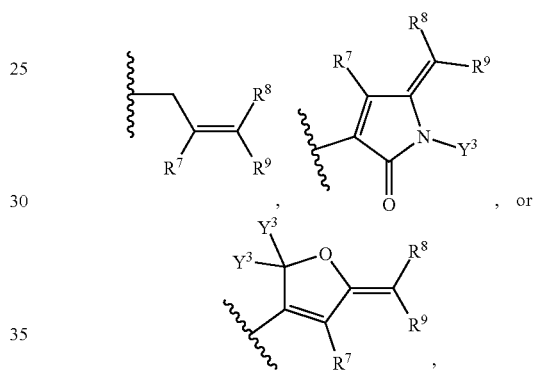

wherein each $Y^3$ is hydrogen, fluoro, chloro, $C_{1-8}$ alkyl, $C_{1-8}$ alkoxy, $C_{1-8}$ heteroalkyl, or $C_{1-8}$ haloalkyl; $R^7$, $R^8$, and $R^9$ are each independently hydrogen or —CN, and at least one of $R^7$, $R^8$, and $R^9$ is —CN.

In some embodiments, A is

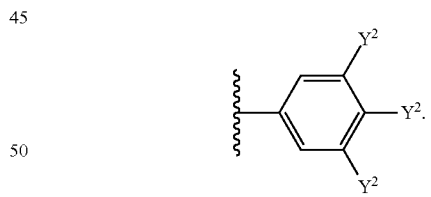

In some embodiments, each $Y^2$ is hydrogen or fluoro. In some embodiments, each $Y^2$ is hydrogen. In some embodiments, each $Y^2$ is fluoro.

In some embodiments, A is

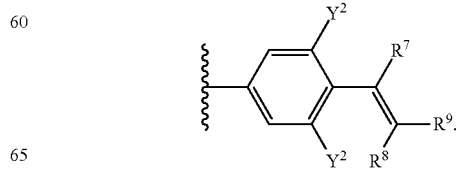

In some embodiments, each $Y^2$ is hydrogen or fluoro. In some embodiments, each $Y^2$ is hydrogen. In some embodiments, each $Y^2$ is fluoro. In some embodiments, $R^7$ is hydrogen, one or both of $R^8$ and $R^9$ are —CN. In some embodiments, $R^7$ is hydrogen, both $R^8$ and $R^9$ are —CN. In some embodiments, each $Y^2$ is hydrogen, $R^7$ is hydrogen, both $R^8$ and $R^9$ are —CN.

In some embodiments, A is

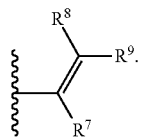

In some embodiments, $R^7$ is hydrogen, one or both of $R^8$ and $R^9$ are —CN. In some embodiments, $R^7$ and $R^8$ are hydrogen, $R^9$ is —CN. In some embodiments, $R^7$ and $R^9$ are hydrogen, $R^8$ is —CN. In some embodiments, $R^7$ is hydrogen, both $R^8$ and $R^9$ are —CN.

In some embodiments, A is and

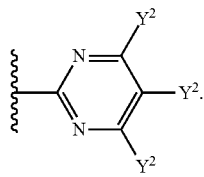

In some embodiments, each $Y^2$ is hydrogen, fluoro or nitro. In some embodiments, each $Y^2$ is hydrogen. In some embodiments, each $Y^2$ is fluoro. In some embodiments, each $Y^2$ is nitro. In some embodiments, A is and

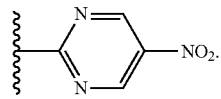

In some embodiments, A is and

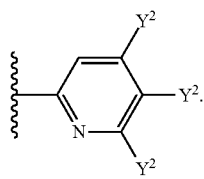

In some embodiments, each $Y^2$ is hydrogen, fluoro or nitro. In some embodiments, each $Y^2$ is hydrogen. In some embodiments, each $Y^2$ is fluoro. In some embodiments, each $Y^2$ is nitro. In some embodiments, A is

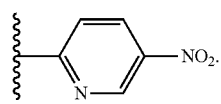

In some embodiments, A is selected from:

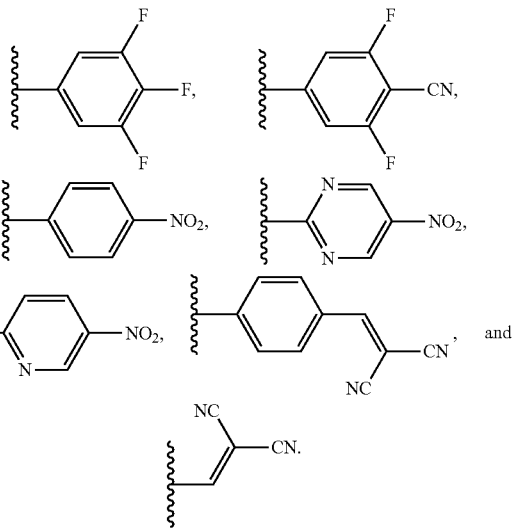

In some embodiments, A is:

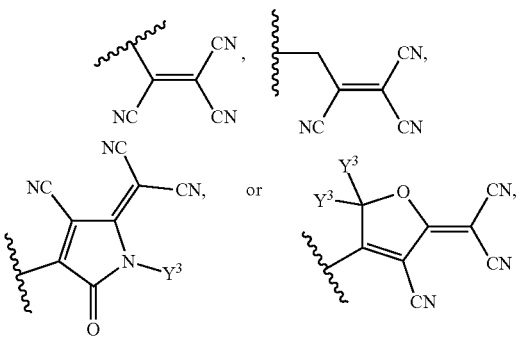

wherein each $Y^3$ is independently hydrogen, fluoro, chloro, $C_{1-8}$ alkyl, $C_{1-8}$ alkoxy, $C_{1-8}$ heteroalkyl, or $C_{1-8}$ haloalkyl.

In some embodiments, each $Y^3$ is $C_{1-8}$ alkyl, $C_{1-8}$ heteroalkyl, or $C_{1-8}$ haloalkyl; $R^7$, $R^8$, and $R^9$ are each independently hydrogen or —CN, and at least one of $R^7$, $R^8$, and $R^9$ is —CN.

In some embodiments, each $Y^3$ is each independently hydrogen, fluoro, chloro, $C_{1-8}$ alkyl, or $C_{1-8}$ haloalkyl. In some embodiments, each $Y^3$ is independently $C_{1-8}$ alkoxy, $C_{1-8}$ heteroalkyl, or $C_{1-8}$ haloalkyl. In some embodiments, each $Y^3$ is each independently perfluorinated $C_{1-8}$ heteroalkyl. In some embodiments, each $Y^3$ is each independently-$CF_3$, —$CF_2CF_3$, or —$CF_2CF_2CF_3$. In some embodiments, each $Y^3$ is each independently-$CF_3$. In some embodiments, each $Y^3$ is methyl. In some embodiments, each $Y^3$ is methyl; $R^7$, $R^8$, and $R^9$ are each independently-CN.

In some embodiments, A is:

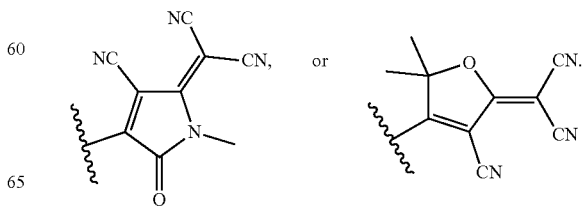

In some embodiments, the nonlinear optical compound has a zwitterionic ground state.

In some embodiments, in the nonlinear optical compound of Formula D-B-A, D is

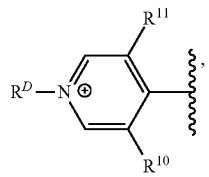

wherein
  wherein $R^{10}$ and $R^{11}$ are each independently hydrogen, fluoro, chloro, or $C_{1-6}$ alkyl; $R^D$ is $C_{1-6}$ alkyl.

In some embodiments, D is

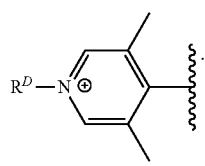

In some embodiments, $R^D$ is methyl, ethyl, n-propyl, n-butyl, n-pentyl, or n-hexyl. In some embodiments, $R^D$ is methyl, ethyl, or n-propyl. In one embodiment, $R^D$ is methyl. In another embodiment, $R^D$ is ethyl. In one preferred embodiment, $R^D$ is n-propyl.

In some embodiments, B is selected from:

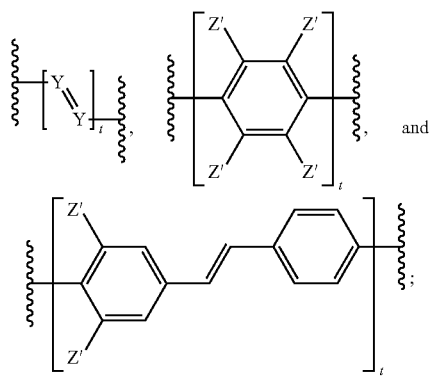

wherein each Y is independently —N= or —CH=, each Z' is independently hydrogen, fluoro, chloro, or methyl, and t is an integer of 1 to 4.

In some embodiments, B is selected from:

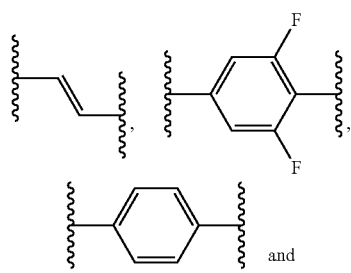

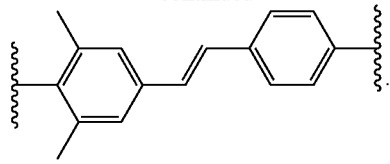

In some embodiments, A is

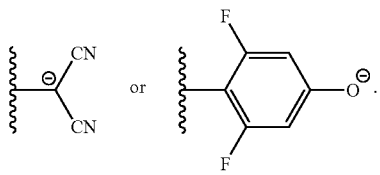 [SMILES: *[C-](C#N)C#N ; *c1c(F)cc([O-])cc1F]

In some embodiments, A is

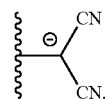

In some embodiments, A is

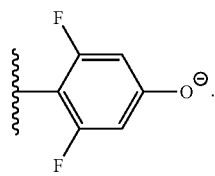 [SMILES: *c1c(F)cc([O-])cc1F]

In some embodiments, the nonlinear optical compound is:

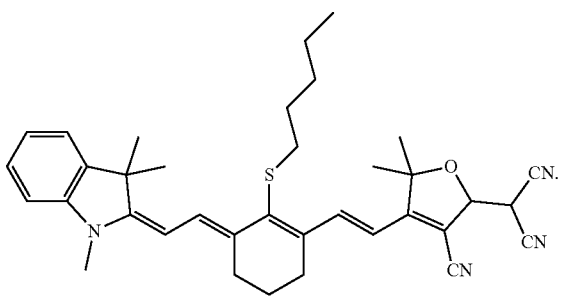 [SMILES: CCCCCSC1=C(/C=C/C2=C(C#N)C(C(C#N)C#N)OC2(C)C)CCC/C1=C\C=C1\N(C)c2ccccc2C1(C)C]

In some embodiments, the nonlinear optical compound is selected from the group consisting of:

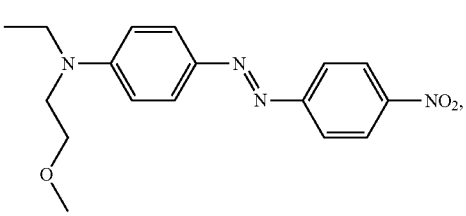

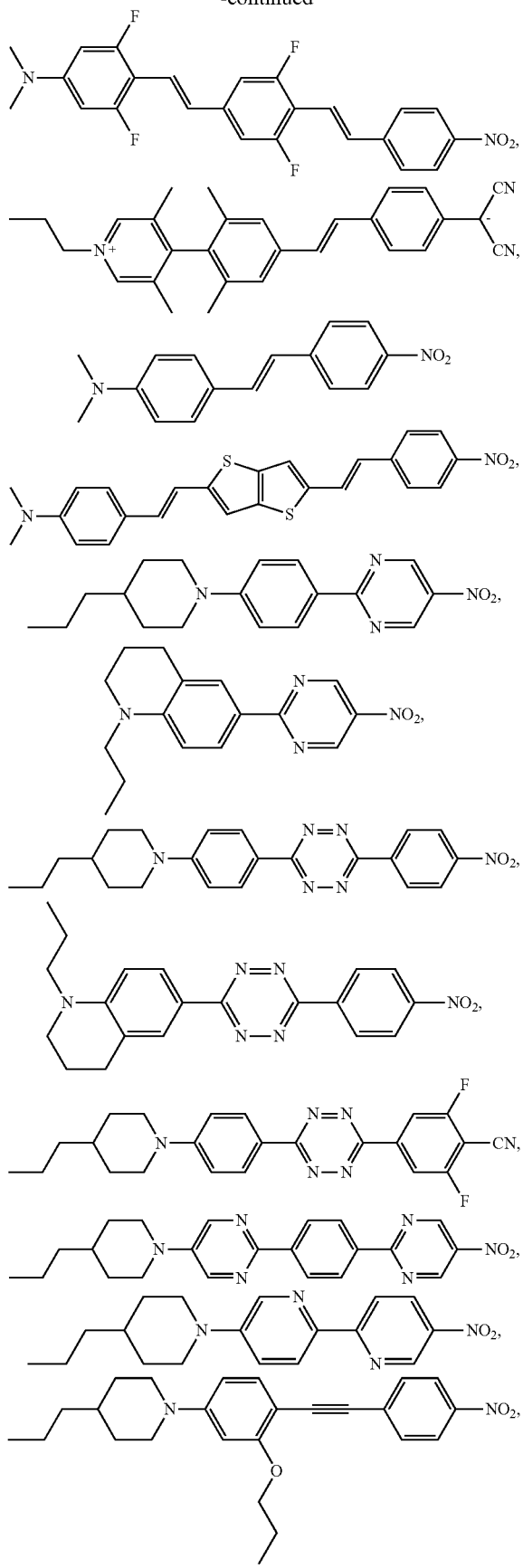

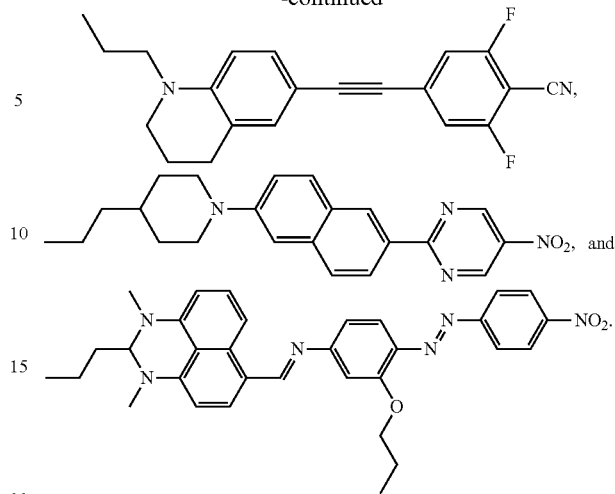

Devices

In another aspect, provided herein are devices comprising a volume comprising the ferroelectric nematic ($N_F$) compositions described herein, e.g., ferroelectric nematic ($N_F$) compositions comprising a ferroelectric nematic host and one or more nonlinear optical compounds (chromophores). In some embodiments, the ferroelectric nematic ($N_F$) compositions spontaneously form a ferroelectric polarization density.

In some embodiments, the device comprises two or more electrodes for application of an electric field. In some embodiments, the electric field causes the ferroelectric polarization density to change in magnitude, thereby producing a change in the electric field. In some embodiments, the polar axis of the ferroelectric polarization density is parallel to the electric field between the electrodes.

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the benzenesulfonamide derivative compounds described herein is P. H. Stahl & C. G. Wermuth "Handbook of Pharmaceutical Salts", Verlag Helvetica Chimica Acta, Zurich, 2002.

EXAMPLES

The examples and embodiments described herein are for illustrative purposes only and various modifications or changes suggested to persons skilled in the art are to be included within the spirit and purview of this application and scope of the appended claims.

Example 1—Mixture A and Mixture B

I. Preparation of the Ferroelectric Nematic ($N_F$) Compositions

Two mixtures, a host mixture (Mixture A) and a host mixture with added dye dopant (Mixture B), were prepared by mixing different host compounds. An azobenzene dye was added to Mixture B. The components in Mixture A and their respective wt % and dipole (D) are summarized in Table 1. The components in Mixture B and their respective wt % and dipole (D) are summarized in Table 2.

TABLE 1

| Mixture A | | | |
|---|---|---|---|
| Component | Compound # | Wt % | Dipole (D) |
| [structure] | 1 | 25 | 19 |
| [structure] | 2 | 25 | 12.3 |
| [structure] | 3 | 25 | 14.4 |
| [structure] | 4 | 25 | 11.4 |

TABLE 2

Mixture B

| Component | Compound # | Wt % | Dipole (D) |
|---|---|---|---|
| [structure: propoxy-methoxy-benzoate linked via ester to dipropoxy-phenyl-benzoate with terminal NO₂] | 1 | 20 | 19 |
| [structure: propyl-phenyl benzoate linked to fluoro-cyano-phenyl ester] | 2 | 20 | 12.3 |
| [structure: pentyl-phenyl benzoate linked to difluoro-cyano-phenyl ester] | 3 | 20 | 14.4 |
| [structure: methoxy-benzoate linked to propoxy-phenyl benzoate with terminal NO₂] | 4 | 20 | 11.4 |
| [structure: ethyl-methoxyethyl-amino-phenyl azo nitrophenyl dye] | 5 | 20 | 14.8 |

The nitro-esters compounds 1 and 4 and the azobenzene dye (compound 5 in Table 2) were synthesized by following the protocols described in literatures including (1) Li et al., *Journal of the American Chemical Society* 143 (42), 17857-17861 (2021); (2) Li et al., *Sci. Adv.* 7, eabf5047 (2021); and (3) Datye et al., *Teinture et Apprets*, 128, 7-31 (1972). Host compounds 2 and 3 were purchased from commercial sources (LCMatter Corp and Ambeed Corp, respectively).

II. Spontaneous Polarization Measurements

Mixture A and Mixture B were filled into ITO-coated liquid crystal cells with a 5 μm gap and a parallel buffed polyimide alignment layer (Instec). A 50V triangle wave was applied to the liquid crystal cells loaded with Mixture A or Mixture B at 25° C. and the polarization switching current was measured.

$N_F$ phase transitions were observed in both Mixture A and Mixture B. The $N_F$ phase transition temperatures and the measured spontaneous polarization of Mixture A and Mixture B are summarized in Table 3.

TABLE 3

| | Phase transitions (° C.) | Spontaneous Polarization (nC/cm^2) |
|---|---|---|
| Mixture A | I-94-N-78-$N_F$ | 3500 |
| Mixture B | I-63-N-45-$N_F$ | 3300 |

Mixture B, which has 20% loading of the azobenzene dye (compound 5) with large hyperpolarizability and a similar dipole as the host mixture (Mixture A), was found to have a $N_F$ phase at room temperature, as evidenced by the polarization switching current measurements. This indicates that the azobenzene dye dopant (compound 5) is highly compatible with the host Mixture A, no disruption of the $N_F$ phase even at a high loading of 20 wt %. The spontaneous polarization measurement of Mixture B was found to be similar to that of the host mixture without the azobenzene dye (Mixture A). The dipole of the azobenzene dye is similar to the dipoles of the $N_F$ host components, based on the dipole values obtained from quantum mechanical calculations (BH&LYP, SVPD, $CH_2Cl_2$). The observed compatibility of the azobenzene dye dopant with the $N_F$ host mixture is consistent with the predicted polar ordering of the dye dopant in the host mixture.

Example 2—Mixture C and Mixture D

I. Preparation of the Ferroelectric Nematic ($N_F$) Compositions

Two mixtures, a host mixture (Mixture C) and a host mixture with added dye dopant (Mixture D), were prepared by mixing different host compounds. A NLO dye was added to Mixture D. The components in Mixture C and their respective wt % and dipole (D) are summarized in Table 4. The components in Mixture D and their respective wt % and dipole (D) are summarized in Table 5.

TABLE 4

| Mixture C | | | |
|---|---|---|---|
| Component | Compound # | Wt % | Dipole (D) |
| [structure] | 1 | 26 | 19 |
| [structure] | 6 | 16 | 11.3 |
| [structure] | 7 | 32 | 14.6 |
| [structure] | 4 | 26 | 11.4 |

TABLE 5

Mixture D

| Component | Compound # | Wt % | Dipole (D) |
|---|---|---|---|
| (structure) | 1 | 25 | 19 |
| (structure) | 6 | 15 | 12.3 |
| (structure) | 7 | 30 | 14.4 |
| (structure) | 4 | 25 | 11.4 |
| (structure) | 8 | 5 | 29.8 |

The nitro-esters compounds 1 and 4 and the cyano-esters compounds 6 and 7 were synthesized by following the protocols described in literatures including (1) Li et al., *Journal of the American Chemical Society* 143 (42), 17857-17861 (2021); 92); (2) Li et al., *Sci. Adv.* 7, eabf5047 (2021); (3) Xianyu, H., Zhao, Y., Gauza, S., Liang, X., & Wu, S.-T. (2008). *Liquid Crystals,* 35 (9), 1129-1135; (4) Li, Jinxing, et al. Giant 11 (2022): 100109.

II. Spontaneous Polarization Measurements $N_F$ phase transitions were observed in both Mixture C and Mixture D and are summarized in Table 6.

TABLE 6

| Mixture | Phase Transition Temperatures |
|---|---|
| Mixture C | I-162-N-132-$N_F$ |
| Mixture D | I-148-N-118-$N_F$ |

Mixture D, which has 5% loading of the NLO dye (Table 5, compound 8) with large hyperpolarizability and a large molecular dipole, was found to have a $N_F$ phase at room temperature, as evidenced by polarization switching current measurements. This indicates that the NLO dye dopant (compound 8) is highly compatible with the host Mixture C with no disruption of the $N_F$ phase. Strong dichroism was observed (dichroic ratio >6) indicating alignment of the long axis of the NLO dye dopant with the $N_F$ director. Measurement of the unpolarized absorption spectrum of Mixture D in a 2 μm parallel buffed sandwich cell is shown in FIG. 1.

III. NLO Dye Synthesis

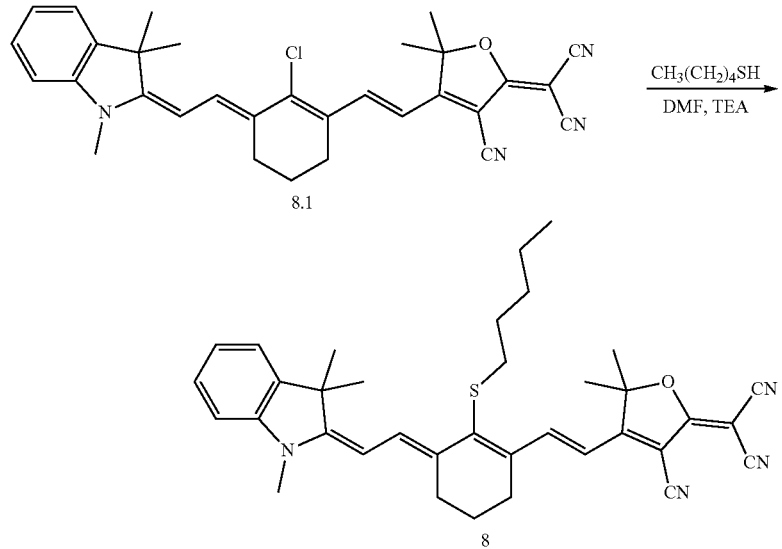

Compound 8 (2-(4-((E)-2-((E)-2-chloro-3-(2-((E)-1,3,3-trimethylindolin-2-ylidene)ethylidene)cyclohex-1-en-1-yl)vinyl)-3-cyano-5,5-dimethylfuran-2 (5H)-ylidene) malononitrile) was synthesized according to literature protocols (Bhuiyan, M. Delower H., et al. "Synthesis, linear & non linear optical (NLO) properties of some indoline based chromophores." Dyes and Pigments 89.2 (2011): 177-187.) and added to a 10 mL round-bottom flask equipped with a stir bar (0.104 g, 170 μmol). N,N-dimethylformamide (12.4 mg, μmol), N-ethyl-N-isopropylpropan-2-amine (26.3 mg, 203 μmol), and pentane-1-thiol (21.2 mg, 203 μmol) were charged were then added, and the flask heated under argon at 60° C. for 16 h. The resulting material was diluted with 10 mL ethyl acetate, washed 5× with 2 mL brine, dry loaded onto silica, and purified via column chromatography (Hexanes/Ethyl acetate 3:1). Further purification was performed by recrystallization from hot IPA to yield a green powder (18 mg).

IV. Electro-Optic Coefficient ($r_{33}$) Measurements

Figure 2:
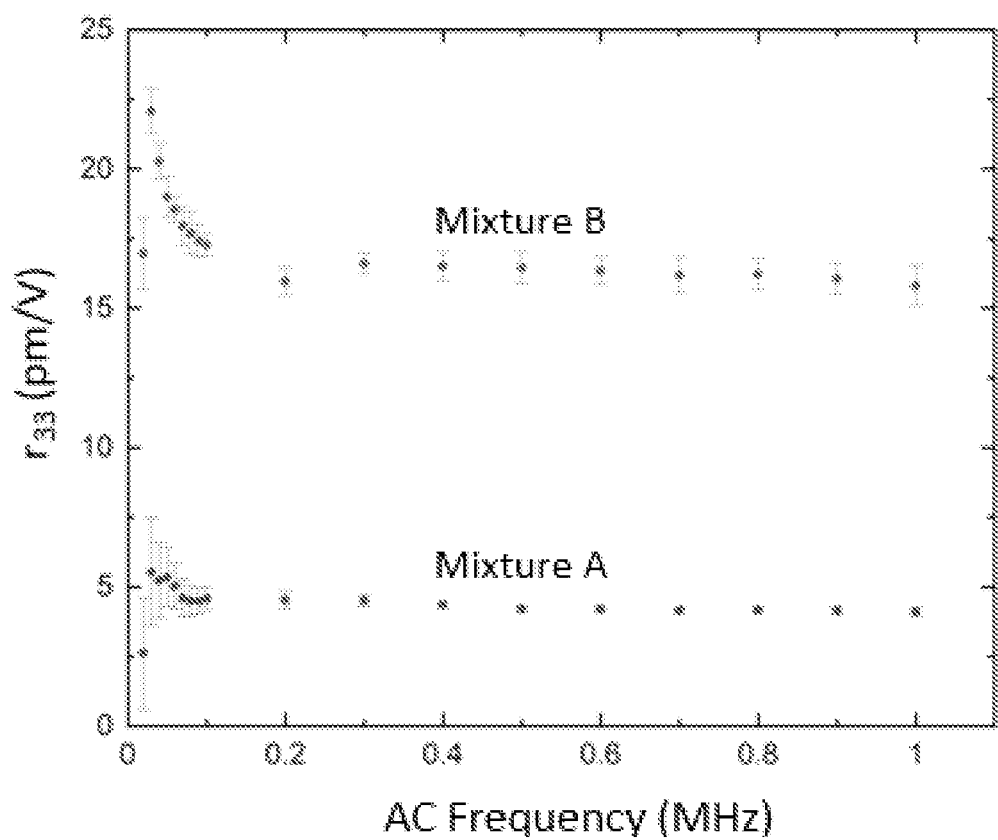
FIG. 2 illustrates a measurement of the electro-optic coefficient ($r_{33}$) of a ferroelectric nematic ($N_F$) composition, with and without a non-linear optical (NLO) dye, in accordance with some embodiments.

Mixture C and Mixture D were filled into custom made cells comprised of a pyrex substrate with in-plane interdigitated gold electrode with a 50 μm gap and a top pyrex cover with a 10 μm gap between them. Measurements of the electro-optic coefficient ($r_{33}$) of mixture C and mixture D were performed at 1550 nm according literature procedures (A. Nahata, C. Wu and J. T. Yardley, *IEEE Transactions on Instrumentation and Measurement*, 41, 128-131, (1992)). The results shown in FIG. 2 show a ~4× increase in the electro-optic coefficient 133 at 1550 nm with addition of 5% of the NLO dye dopant (compound 8) at frequencies >0.1 MHz where the electro-optic response is dominated by the second order nonlinear optical susceptibility. This shows evidence of polar ordering of the dye occurring spontaneously by mixing with the host mixture.

What is claimed is:

1. A ferroelectric nematic ($N_F$) composition comprising a ferroelectric nematic host and a nonlinear optical compound having a formula of: D-B-A, wherein D is a donor moiety, B is a π-conjugated bridging moiety, and A is an acceptor moiety; wherein the second order nonlinear optical (NLO) coefficient of the nonlinear optical compound is higher than the NLO coefficient of the $N_F$ host.

2. The ferroelectric nematic composition of claim 1, wherein the spontaneous polarization (Ps) of the ferroelectric nematic composition is greater than about 1 μC/cm^2.

3. The ferroelectric nematic composition of claim 1, wherein the NLO coefficient of the $N_F$ host is greater than 0.1, 0.2, 0.3, 0.4, 0.5, 0.6, 0.7, 0.8, 0.9, or 1 pm/V.

4. The ferroelectric nematic composition of claim 1, wherein the $N_F$ host comprises a compound of Formula (I):

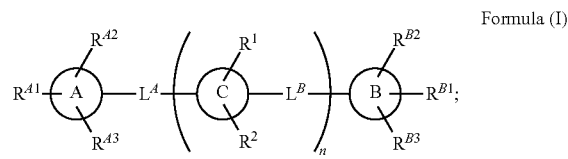

wherein ring A, ring B, and each ring C are independently an aryl; $L^A$ and each $L^B$ are each independently a bond, —N=N—, or

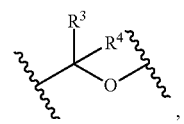

wherein $R^3$ and $R^4$ are each fluoro or $R^3$ and $R^4$ form an oxo;

$R^1$ and $R^2$ are each independently hydrogen, fluoro, or $C_{1-6}$ alkoxy;

$R^{A1}$ is hydrogen, $C_{1-6}$ alkyl, $C_{1-6}$ alkoxy, $C_{1-6}$ heteroalkyl, or

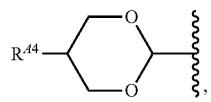

wherein
$R^{A4}$ is $C_{1-6}$ alkyl;
$R^{A2}$ and $R^{A3}$ are each independently hydrogen, fluoro, or —OR, wherein R is $C_{1-6}$ alkyl optionally substituted with a $C_{1-6}$ alkoxy;
$R^{B1}$ is fluoro, —NO$_2$, or —CN;
$R^{B2}$ and $R^{B3}$ are each independently hydrogen, fluoro, or methoxy; and
n is an integer of 1 to 8;
provided at least one of $L^A$ and $L^B$ is not a bond.

5. The ferroelectric nematic composition of claim 4, wherein the compound of Formula (I) has a structure of Formula (Ia):

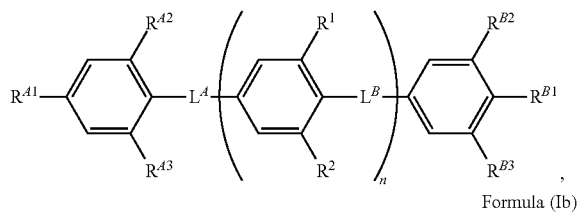
Formula (Ia)

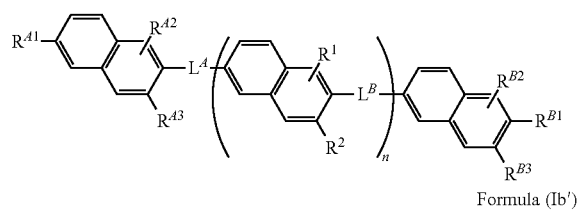
Formula (Ib)

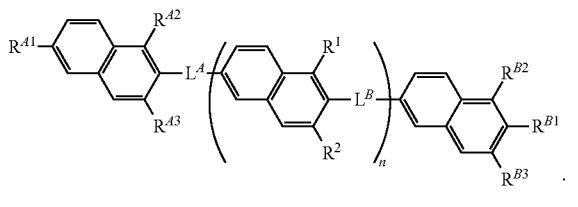
Formula (Ib')

6. The ferroelectric nematic composition of claim 4, wherein

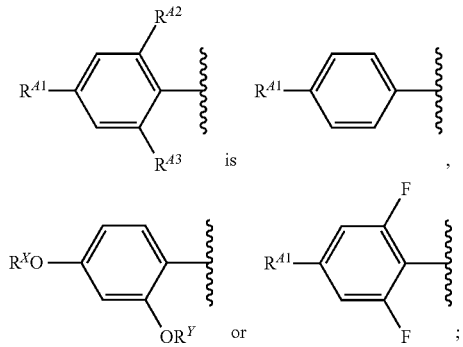
is $R^{A1}$ is $C_{1-6}$ alkyl or

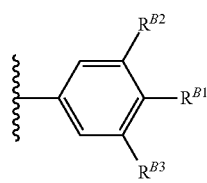
;

$R^X$ is $C_{1-6}$ alkyl and $R^Y$ is $C_{1-6}$ alkyl optionally substituted with methoxy; wherein

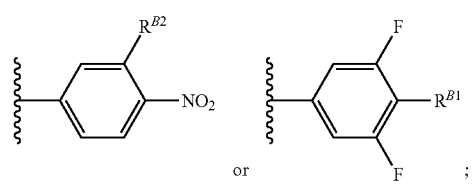

is optionally $R^{B2}$ is hydrogen or fluoro, and $R^{B1}$ is —CN or F.

7. The ferroelectric nematic composition of claim 4, wherein the compound of Formula (I) comprises:

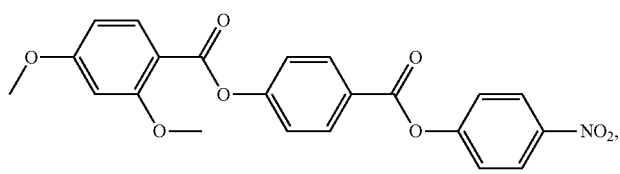

-continued
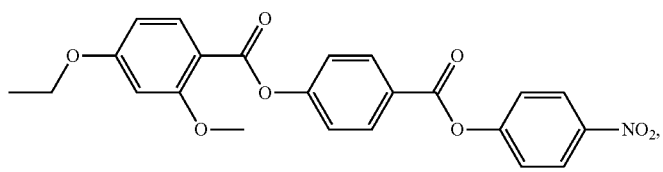
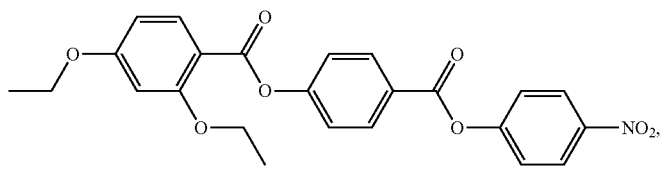
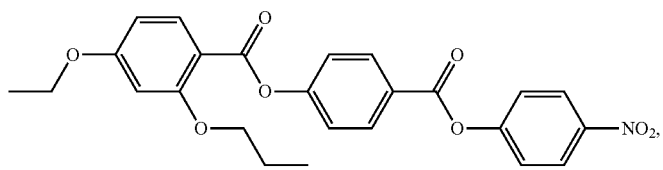
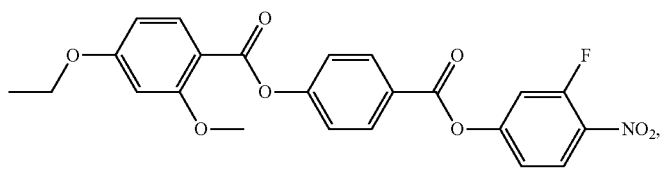
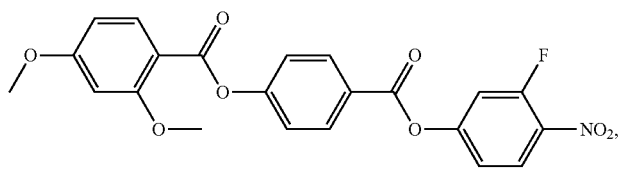
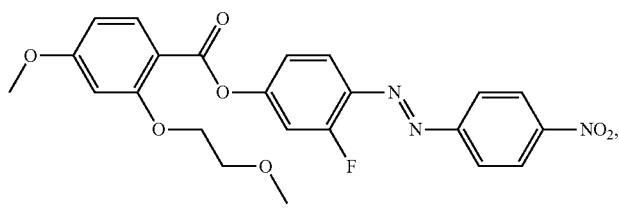
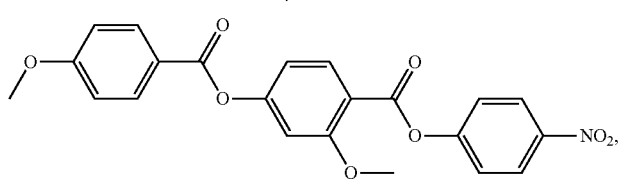
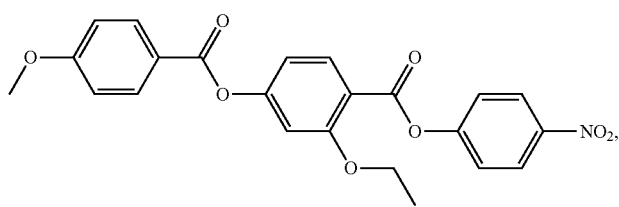
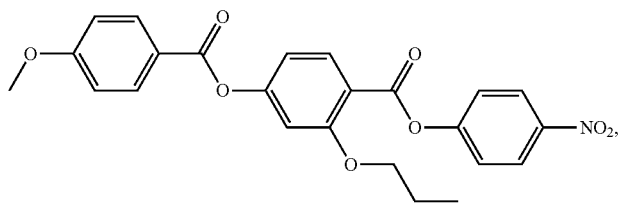

-continued
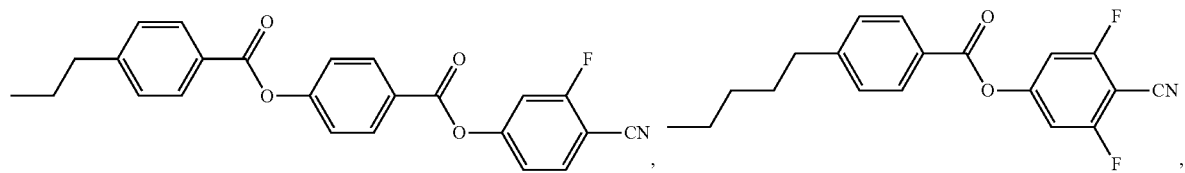
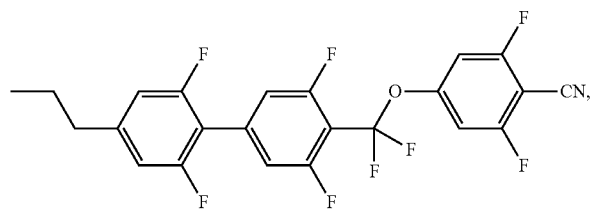
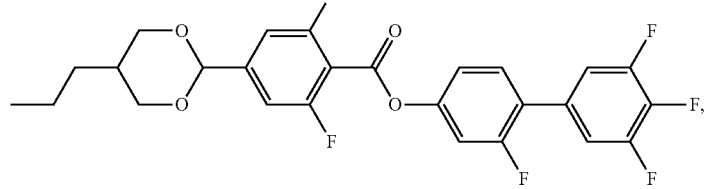
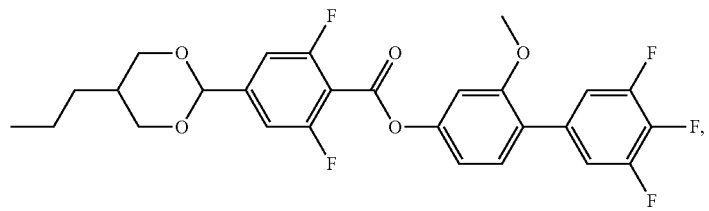
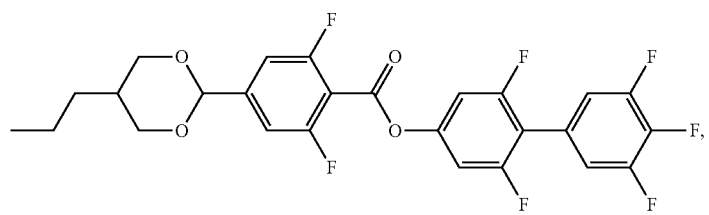
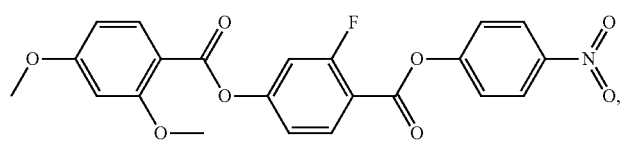
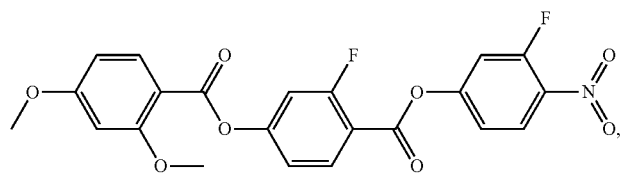
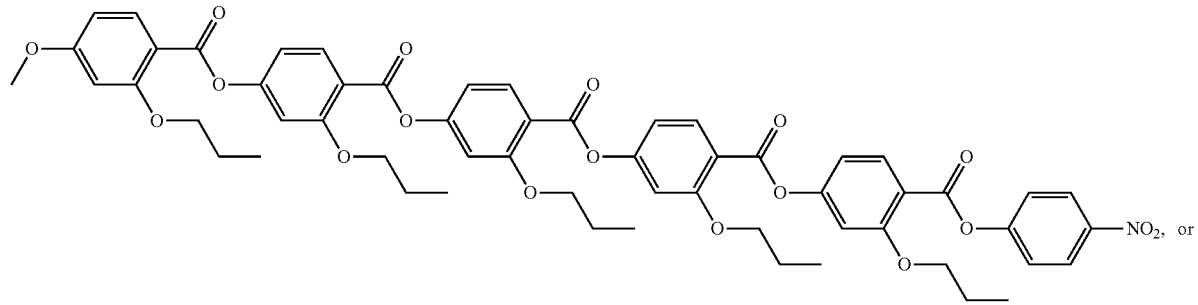

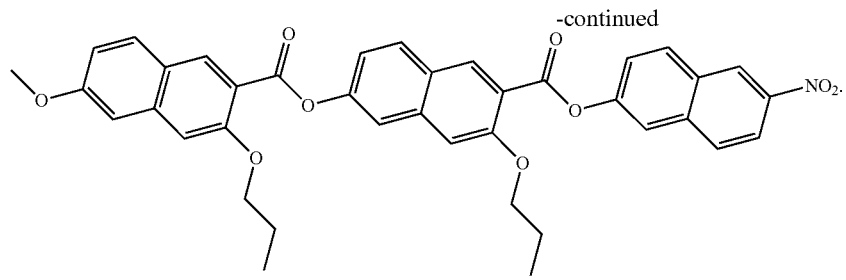

8. The ferroelectric nematic composition of claim 1, wherein the nonlinear optical compound has a neutral ground state.

9. The ferroelectric nematic composition of claim 1, wherein in the nonlinear optical compound of Formula D-B-A, D is

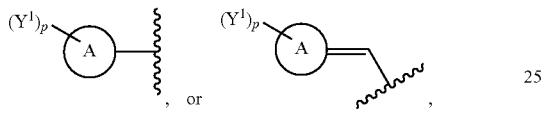

wherein Ring A is an aryl, heterocyclyl, or heteroaryl ring, each $Y^1$ is independently -OH, fluoro, $NR^5R^6$, $C_{1-8}$ cycloalkyl, or $C_{1-6}$ alkoxy, wherein $R^5$ and $R^6$ are each independently hydrogen or $C_{1-6}$ alkyl;

p is an integer of 0 to 5.

10. The ferroelectric nematic composition of claim 9, wherein in the nonlinear optical compound of Formula D-B-A, B is selected from:

a bond,

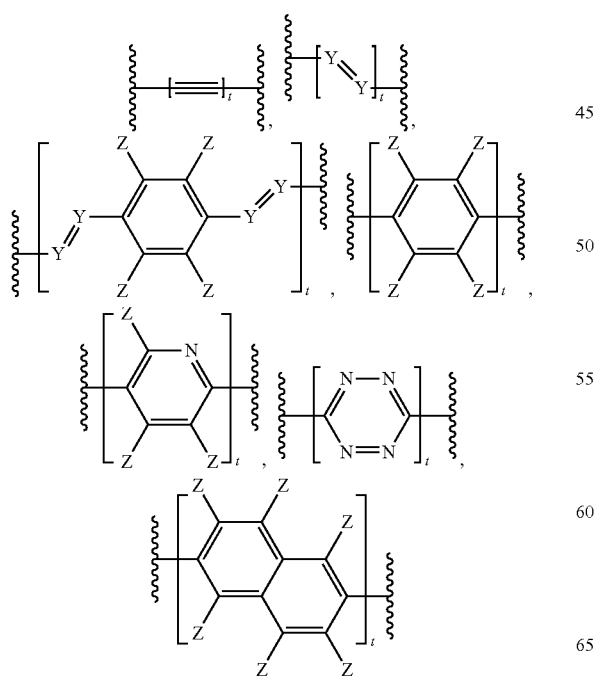

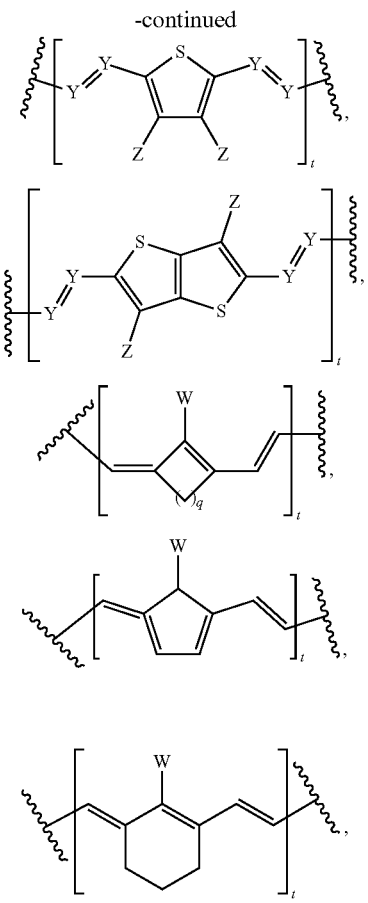

and a combination thereof;

wherein each Y is independently —N= or —CH=, each Z is independently hydrogen, fluoro, chloro, or $C_{1-6}$ alkoxy, W is hydrogen, fluoro, chloro, $C_{1-8}$ alkyl, $C_{1-8}$ alkoxy, $C_{1-8}$ heteroalkyl, or $C_{1-8}$ haloalkyl, q is an integer of 0 to 5, and t is an integer of 1 to 5.

11. The ferroelectric nematic composition of claim 9, wherein B is selected from:

a bond,

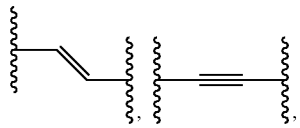

73
-continued

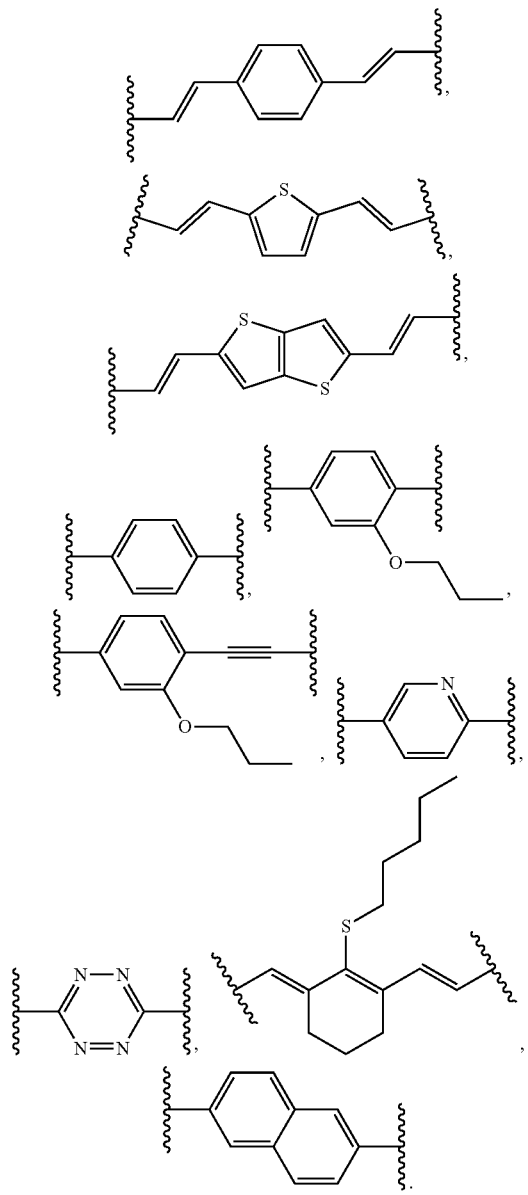

12. The ferroelectric nematic composition of claim 9, wherein in the nonlinear optical compound of Formula D-B-A, A is selected from:

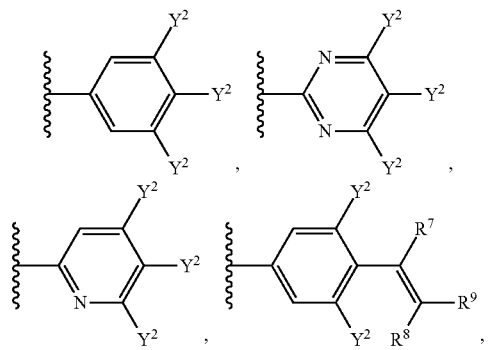

74
-continued

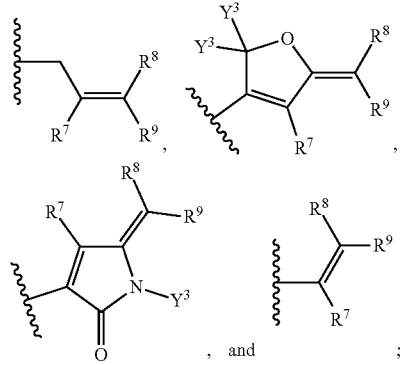

wherein each $Y^2$ is hydrogen, fluoro, chloro, —NO$_2$, —CN, —NCS, SO$_2$CH$_3$, or SO$_2$CF$_3$; each $Y^3$ is independently hydrogen, fluoro, chloro, C$_{1-8}$ alkyl, C$_{1-8}$ alkoxy, C$_{1-8}$ heteroalkyl, or C$_{1-8}$ haloalkyl; $R^7$, $R^8$, and $R^9$ are each independently hydrogen or —CN, and at least one of $R^7$, $R^8$, and $R^9$ is —CN.

13. The ferroelectric nematic composition of claim 12, wherein A is selected from:

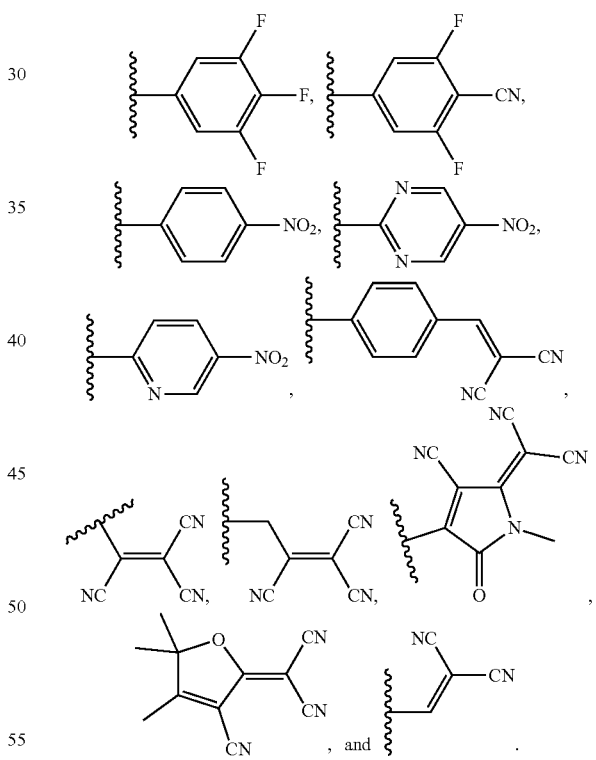

14. The ferroelectric nematic composition of claim 1, wherein D is selected from:

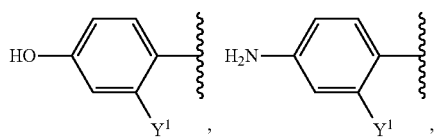

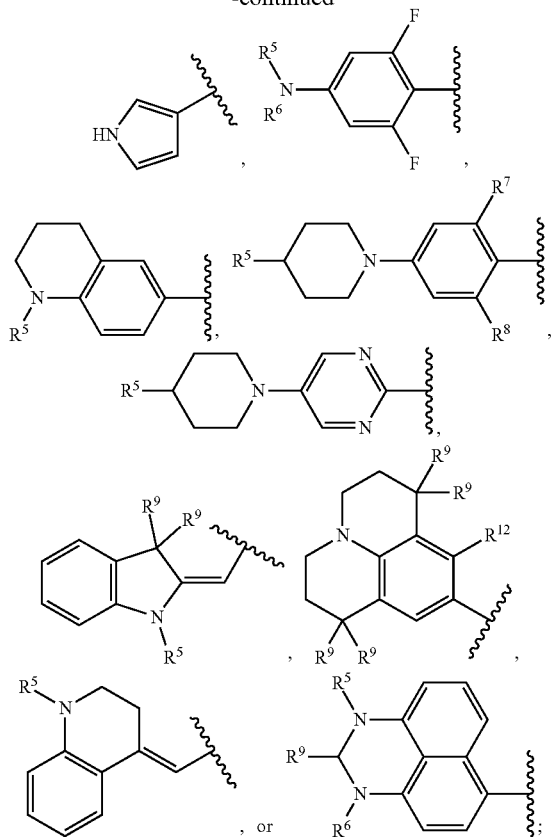

wherein $R^5$, $R^6$ and $R^9$ are each independently hydrogen or $C_{1-6}$ alkyl, $R^7$ and $R^8$ are each independently hydrogen or $C_{1-6}$ alkoxy, and $R^{12}$ is hydrogen, $C_{1-10}$ alkyl, $C_{1-10}$ heteroalkyl, —O—$C_{1-10}$ alkyl, —O—$C_{1-10}$ heteroalkyl, —O—$C_{0-9}$ alkylene-$C_{6-10}$ aryl, —O—$C_{0-9}$ alkylene-$C_{1-10}$ heteroaryl, or —$NR^5R^6$, wherein D is optionally

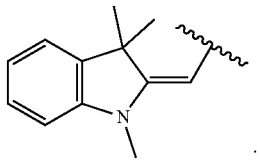 [SMILES: */C=C1/N(C)c2ccccc2C1(C)C]

15. The ferroelectric nematic composition of claim 1, wherein the nonlinear optical compound has a zwitterionic ground state.

16. The ferroelectric nematic composition of claim 1, wherein the nonlinear optical compound is selected from the group consisting of:

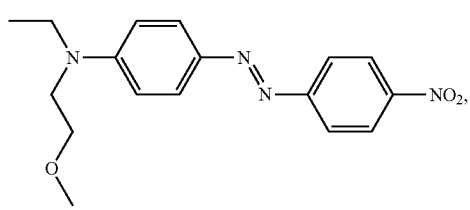

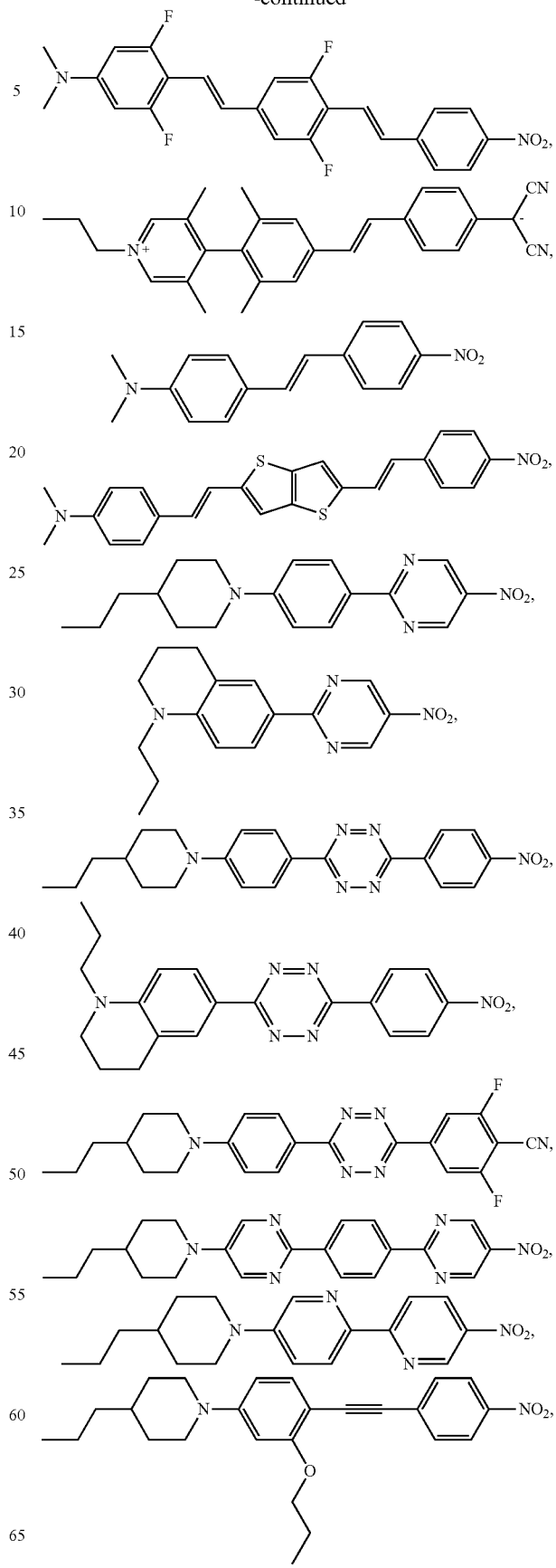

-continued

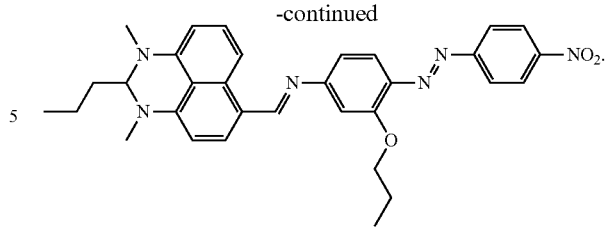

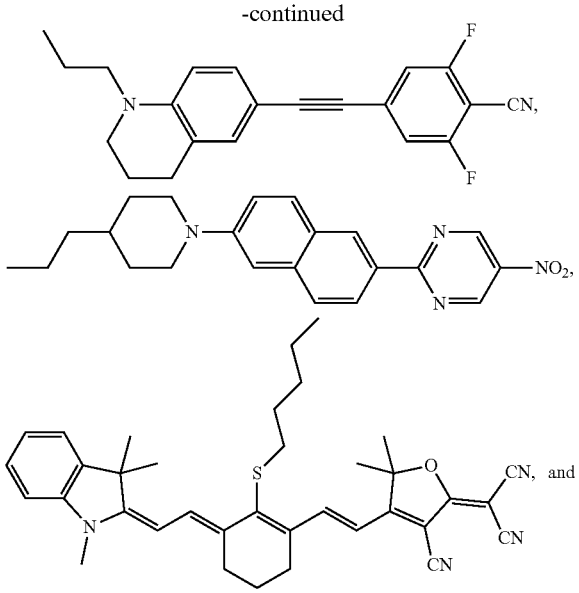

17. The ferroelectric nematic composition of claim 1, wherein the ferroelectric nematic ($N_F$) composition comprises between about 1% to about 30% w/w nonlinear optical compound(s).

18. A device comprising the ferroelectric nematic composition of claim 1.

19. The device of claim 18, wherein the device comprises two or more electrodes.

20. The device of claim 19, an electric field is applied between the electrodes and across the ferroelectric nematic composition within the device.

* * * * *